(12) United States Patent
Lala et al.

(10) Patent No.: US 12,358,984 B2
(45) Date of Patent: Jul. 15, 2025

(54) METHODS FOR TREATING CANCER WITH ANTI-PD-1 ANTIBODIES

(71) Applicant: Merck Sharp & Dohme LLC, Rahway, NJ (US)

(72) Inventors: Mallika Lala, West New York, NY (US); Lokesh Jain, Edison, NJ (US); Mengyao Li, Springfield, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 47 days.

(21) Appl. No.: 16/966,968

(22) PCT Filed: Feb. 8, 2019

(86) PCT No.: PCT/US2019/017177
§ 371 (c)(1),
(2) Date: Aug. 3, 2020

(87) PCT Pub. No.: WO2019/160751
PCT Pub. Date: Aug. 22, 2019

(65) Prior Publication Data
US 2021/0047408 A1    Feb. 18, 2021

Related U.S. Application Data

(60) Provisional application No. 62/732,828, filed on Sep. 18, 2018, provisional application No. 62/630,038, filed on Feb. 13, 2018.

(51) Int. Cl.
| | | |
|---|---|---|
| *A61P 35/00* | (2006.01) | |
| *A61K 39/395* | (2006.01) | |
| *A61K 47/22* | (2006.01) | |
| *A61K 47/26* | (2006.01) | |
| *C07K 16/28* | (2006.01) | |
| *A61K 39/00* | (2006.01) | |

(52) U.S. Cl.
CPC .... *C07K 16/2818* (2013.01); *A61K 39/39541* (2013.01); *A61K 47/22* (2013.01); *A61K 47/26* (2013.01); *A61P 35/00* (2018.01); *A61K 2039/505* (2013.01); *A61K 2039/545* (2013.01); *C07K 2317/51* (2013.01); *C07K 2317/515* (2013.01); *C07K 2317/56* (2013.01)

(58) Field of Classification Search
CPC ............ C07K 16/2828; C07K 2317/51; C07K 2317/515; C07K 2317/56; A61P 35/00; A61K 39/39541; A61K 47/22; A61K 47/26; A61K 2039/505; A61K 2039/545
See application file for complete search history.

(56) References Cited

U.S. PATENT DOCUMENTS

| | | | |
|---|---|---|---|
| 9,220,776 B2 † | 12/2015 | Sharma | |
| 2016/0022814 A1 | 1/2016 | Petit et al. | |
| 2017/0313775 A1 † | 11/2017 | Diaz | |
| 2020/0109204 A1 * | 4/2020 | Edwards | A61P 35/00 |

FOREIGN PATENT DOCUMENTS

| | | |
|---|---|---|
| JP | 2017530950 A | 10/2017 |
| MX | 2019002946 A | 9/2019 |
| MX | 2019008207 A | 12/2019 |
| WO | 2008156712 A1 | 12/2008 |
| WO | 2012135408 A1 | 10/2012 |
| WO | 2014100079 A1 | 6/2014 |
| WO | 2015095423 A2 | 6/2015 |
| WO | 2016032927 A1 | 3/2016 |
| WO | 2016137850 A1 | 9/2016 |
| WO | 2016/176504 A1 † | 11/2016 |
| WO | 2016196389 A1 | 12/2016 |
| WO | 2017106656 A1 | 6/2017 |
| WO | 2017/127811 A1 † | 7/2017 |
| WO | 2017151502 A1 | 9/2017 |
| WO | WO-2017165125 A1 * | 9/2017 |
| WO | 2017/205216 A1 † | 11/2017 |
| WO | 2017197263 A1 | 11/2017 |
| WO | 2017/210624 A1 † | 12/2017 |
| WO | 2018053106 A1 | 3/2018 |

(Continued)

OTHER PUBLICATIONS

Ahmadzadeh et al., Tumor antigen-specific CD8 T cells infiltrating the tumor express high levels of PD-1 and are functionally impaired, Blood, 2009, 1537-1544, 114.

Baert et al., Influence of Immunogenicity on the long term efficacy of Infliximab in Crohns disease, New England Journal Med., 2003, pp. 601-608, 348.

Beniaminovitz et al., Prevention of rejection in cardiac transplantation by blockade of the interleukin 2 receptor with a monoclonal antibody, New England Journal of Medicine, 2000, pp. 613-619, 342.

Brahmer et al., Safety and Activity of Anti-PD-L1 Antibody in Patients with Advanced Cancer, the New England Journal of Medicine, 2012, pp. 2455-2465, vol. 366, No. 26.

(Continued)

*Primary Examiner* — Mark Halvorson
*Assistant Examiner* — Dennis J Sullivan
(74) *Attorney, Agent, or Firm* — Patrick Rehfuss; Alysia A. Finnegan

(57) ABSTRACT

The present invention relates to methods for treating cancer in a patient comprising administering a PD-1 antagonist, e.g., an anti-PD-1 antibody or antigen binding fragment thereof (e.g. pembrolizumab), in specific amounts to the patient about every six weeks. In some embodiments, the amount of anti-PD-1 antibody or antigen binding fragment thereof is about 400 mg. In certain embodiments, the PD-1 antagonist is pembrolizumab, or an antigen binding fragment thereof. Also provided are compositions and kits comprising a dosage of an anti-PD-1 antibody, or antigen-binding fragment thereof, and uses thereof for treating cancer.

28 Claims, 5 Drawing Sheets

Specification includes a Sequence Listing.

(56) References Cited

FOREIGN PATENT DOCUMENTS

WO 2018129559 A1 7/2018

OTHER PUBLICATIONS

Chen et al., PD-L1 Expression is Characteristic of a Subset of Aggressive B-cell Lymphomas and Virus-Associated Malignancies, Clinical Cancer Research, 2013, pp. 3462-3473, vol. 19.
Dang, T.O. et al., Pembrolizumab for the treatment of PD-LI positive advanced or metastatic non-small cell lung cancer, Expert Review of Anticancer Therapy, 2015, 1-23, 11:43.
Dong et al., Tumor-associated B7-H1 promotes T-cell apoptosis: A potential mechanism of immune evasion, Nature Medicine, 2002, pp. 793-800, vol. 8(8).
Freshwater, T. et al., Evaluation of dosing strategy for pembrolizumab for oncology indications, Journal for ImmunoTherapy of Cancer, 2017, 1-9, 5:43.
Gadiot et al., Overall Survival and PD-L1 Expression in Metastasized Malignant Melanoma, Cancer, 2011, 2192-2201, 117.
Gao et al., Overexpression of PD-L1 Significantly Associates with Tumor Aggressiveness and Postoperative Recurrence in Human Hepatocellular Carcinoma, Clinical Cancer Research, 2009, 971-979, 15.
Garon et al., Pembrolizumab for the Treatment of Non-Small-Cell Lung Cancer, the New England Journal of Medicine, 2015, pp. 2018-2028, vol. 372, No. 21.
Ghebeh et al., FOXP3+ Tregs and B7-H1+/PD-1+T lymphocytes co-infiltrate the tumor tissues of high-risk breast cancer patients: Implication for immunotherapy, BMC Cancer, 2008, 57-68, 8.
Ghebeh et al., The B7-H1 (PD-L1) T Lymphocyte-Inhibitory Molecule Is Expressed in Breast Cancer Patients with Infiltrating Ductal Carcinoma: Correlation with Important High-Risk Prognostic Factors, Neoplasia, 2006, 190-198, 8.
Ghosh et al., Natalizumab for active Crohns disease, New England J. Med., 2003, pp. 24-32, 348.
Hamanishi et al., Programmed cell death 1 ligand 1 and tumor-infiltrating CD8+ T lymphocytes are prognostic factors of human ovarian cancer, Proceedings of the National Academy of Sciences USA, 2007, 3360-3365, 104.
Hamid et al., Safety and Tumor Responses with Lambrolizumab (Anti-PD-1) in Melanoma, New Eng. J. Med., 2013, 134-144, 369(2).
Hino et al., Tumor cell expression of programmed cell death-1 ligand 1 is a prognostic factor for malignant melanoma, Cancer, 2010, 1757-1766, 116(7).
Inman et al., PD-L1 (B7-H1) expression by urothelial carcinoma of the bladder and BCG-induced granulomata: associations with localized stage progression, Cancer, 2007, 1499-1505, 109.
Lipsky et al., Infliximab and methotrexate in the treatment of rheumatoid arthritis, New England Journal of Medicine, 2000, pp. 1594-1602, 343.
Milgrom et al., Treatment of allergic asthma with monoclonal anti IgE antibody, New England Journal Med., 1999, pp. 1966-1973, 341.
Nakanishi et al., Overexpression of B7-H1 (PD-L1) significantly associates with tumor grade and postoperative prognosis in human urothelial cancers, Cancer Immunol. Immunother., 2007, 1173-1182, 56.
Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.
Ohigashi et al., Clinical Significance of Programmed Death-1 Ligand-1 and Programmed Death-1 Ligand-2 Expression in Human Esophageal Cancer, Clin. Cancer Research, 2005, 2947-2953, 11.
Robert et al., Anti-programmed-death-receptor-1 treatment with pembrolizumab in ipilimumab-refractory advanced melanoma: a randomised dose-comparison cohort of a phase 1 trial, the Lancet, 2014, pp. 1109-1117, vol. 384.
Robert et al., Nivolumab in Previously Untreated Melanoma without BRAF Mutation, the New England Journal of Medicine, 2015, pp. 320-330, vol. 372, No. 4.
Robert et al., Pembrolizumab versus Ipilimumab in Advanced Melanoma, the New England Journal of Medicine, Jun. 25, 2015, pp. 2521-2532, 372.
Sharpe et al., The function of programmed cell death 1 and its ligands in regulating autoimmunity and infection, Nature Immunology, 2007, 239-245, 8.
Shimauchi et al., Augmented expression of programmed death-1 in both neoplastic and non-neoplastic CD4+ T-cells in adult T-cell leukemia/lymphoma, Int. J. Cancer, 2007, 2585-2590, 121.
Slamon et al., Use of chemotherapy plus a monoclonal antibody against HER2 for metastatic breast cancer that overexpresses HER2, New England J. Med., 2001, pp. 783-792, 344.
Taube, et al., Colocalization of inflammatory response with B7-H1 expression in humna melanocytic lesions supports an adaptive resistance mechanism of ummune escape, Sci Transl Med, 2012, pp. 127ra37, vol. 4.
Thompson et al., Costimulatory B7-H1 in renal cell carcinoma patients: Indicator of tumor aggressiveness and potential therapeutic target, Proc. Nat'l Acad. Sci. USA, 2004, 17174-17179, 101(49).
Thompson et al., PD-1 Is Expressed by Tumor-Infiltrating Immune Cells and Is Associated with Poor Outcome for Patients with Renal Cell Carcinoma, Clinical Cancer Research, 2007, pp. 1757-1761, vol. 15.
Thompson et al., Significance of B7-H1 Overexpression in Kidney Cancer, Cancer, 2006, 206-211, 5.
Thompson et al., Tumor B7-H1 Is Associated with Poor Prognosis in Renal Cell Carcinoma Patients with Long-Term Follow-up, Cancer Res., 2006, pp. 3381-3385, vol. 66.
Topalian et al., Safety, Activity, and Immune Correlates of Anti-PD-1 Antibody in Cancer, New Eng. J. Med., 2012, 2443-2454, 366(26).
Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.
Weber, Wolfgang A., Assessing Tumor Response to Therapy, Journal of Nuclear Medicine, 2009, 1S-10S, 50.
WHO Drug Information, vol. 27, No. 2, pp. 161-162 (2013).
Wolchok et al., Nivolumab plus Ipilimumab in Advanced Melanoma, the New England Journal of Medicine, 2013, pp. 122-133, vol. 369(2).
Yang et al., PD-L1: PD-1 Interaction Contributes to the Functional Suppression of T-Cell Responses to Human Uveal Melanoma Cells In Vitro, Invest Ophthalmol Vis Sci, 2008, 2518-2525, 49(6).
Zhao et al., A Model-Based Exposure-Response (E-R) Assessment of a Nivolumab (NIVO) 4-Weekly (Q4W), AACR, 2017.
Zhao, X. et al., Abstract CT101: A model-based exposure-response (E-R) assessment of a nivolumab (NIVO) 4-weekly (Q4W) dosing schedule across multiple tumor types, AACR, 2017, 1-4, N/A.
Castellino, Alexander M., Pembrolizumab Flat Dosing Wastes Nearly $1 Billion Annually, Medscape Medical NewsConference NewsAmerican Society of Clinical Oncology (ASCO) 2017 Annual Meeting, 2017, 1-3, N/A.
Elassaiss-Schaap, J. et al., Using Model-Based "Learn and Confirm" to Reveal the Pharmacokinetics-Pharmacodynamics Relationship of Pembrolizumab in the Keynote-001 Trial : Modeling of the PK/PD of Pembro in Keynote-001, CPT Pharmacometrics Syst. Pharmacol., 2017, 21-28, 6(1).
Goldstein, Daniel A. et al., A phamacoeconomic analysis of personalized dosing versus fixed dosing of pembrolizumab in first-line PD-LI positive non-small cell lung cancer, Journal of Clinical Oncology, 2017, Abstract 9013, 35 (Suppl. 15).
Lala, Mallika et al., A six-weekly dosing schedule for pembrolizumab in patients with cancer based on evaluation using modelling and simulation, European Journal of Cancer, 2020, 68-75, 131.
Walker, Scott et al., Dosing and Timing of Immuno-Oncology Drugs, CADTH Technology Review: Optimal Use 360 Report, 2019, 1-50, 25.

(56) References Cited

OTHER PUBLICATIONS

Ott, Patrick A. et al., Safety and Antitumor Activity of Pembrolizumab in Advanced Programmed Death Ligand 1-Positive Endometrial Cancer: Results From the Keynote-028 Study, J Clin Oncol, 2017, 2535-2541, 35(22).

Pembrolizumab (Rx). Medscape. Sep. 18, 2017. found on Aug. 30, 2022, URL: https://web.archive.org/web/20170918010806/http://reference.medscape.com/drug/keytruda-pembrolizumab-999962 (5 pages).

Kwok, Gerry et al., Pembrolizumab (Keytruda), Human Vaccines & Immunotherapeutics, 2016, 2777-2789, 12:11.

Cooper, L J et al., Role of heavy chain constant domains in antibody-antigen interaction. Apparent specificity differences among streptococcal IgG antibodies expressing identical variable domains, J Immunol, 150(6), 2231-2242, 1993.

Liang, Wei-Ching et al., Dramatic activation of an antibody by a single amino acid change in framework, Scientific Reports, 11:22365, 1-9, 2021.

McDermott, et al., PD-1 as a potential target in cancer therapy, Cancer Medicine, pp. 662-673, 2013, WO.

Montano, R.F. et al., Influence of the isotype of the light chain on the properties of IgG, the Journal of Immunology, 168, 224-231, 2002.

A. Baumann, Early Development of Therapeutic Biologics—Pharmacokinetics, Current Drug Metabolism, 7, 15-21, 2006.

Agoram, Balaji M. et al., The role of mechanism-based pharmacokinetic-pharmacodynamic (PK-PD) modelling in translational research of biologics, Drug Discovery Today, 12(23/24), 1018-1024, 2007.

Ahamadi, M. et al., Model-Based Characterization of the Pharmacokinetics of Pembrolizumab: A Humanized Anti-PD-1 Monoclonal Antibody in Advanced Solid Tumor, CPT Pharmacometrics Syst. Pharmacol., 6, 49-57, 2017.

Azanza, J-R et al., Monoclonal antibodies: Pharmacokinetics as a basis for new dosage regimens?, J Oncol Pharm Practice, 0(0), 1-7, 2014.

Bai, Shuang et al., A Guide to Rational Dosing of Monoclonal Antibodies, Clin Pharmacokinet, 51(2), 119-135, 2012.

Baselga, J. et al., Phase I Studies of Anti-Epidermal Growth Factor Receptor Chimeric Antibody C225 Alone and in Combination With Cisplatin, J Clin Oncol, 18, 904-914, 2000.

Baxter, Laurence T. et al., Biodistribution of Monoclonal Antibodies: Scale-up from Mouse to Human Using a Physiologically Based Pharmacokinetic Model, Cancer Research, 55, 4611-4522, 1995.

Bruno, Rene et al., Population pharmacokinetics of trastuzumab in patients With HER2+ metastatic breast cancer, Cancer Chemother Pharmacol, 56, 361-369, 2005.

CADTH, Dosing and Timing of Immuno-Oncology Drugs, CADTH, N/A, 3 pages, 2020.

Cao, Yanguang et al., Second-generation minimal physiologically-based pharmacokinetic model for monoclonal antibodies, J Pharmacokinet Pharmacodyn, 40, 597-607, 2013.

Center for Drug Evaluation and Research, Clinical Pharmacology and Biopharmaceutics Review(s), Center for Drug Evaluation and Research, N/A, 1-43, 2014.

Chatterjee, M. et al., Systematic evaluation of pembrolizumab dosing in patients with advanced non-small-cell lung cancer, Annals of Oncology, 27, 1291-1298, 2015.

Chatterjee, MS et al., Population Pharmacokinetic/Pharmacodynamic Modeling of Tumor Size Dynamics in Pembrolizumab-Treated Advanced Melanoma, CPT Pharmacometrics Syst. Pharmacol., 6, 29-39, 2017.

De Greef, R. et al., Pembrolizumab: Role of Modeling and Simulation in Bringing a Novel Immunotherapy to Patients With Melanoma, CPT Pharmacometrics Syst. Pharmacol., 6, 5-7, 2017.

Dirks, Nathanael L. et al., Population Pharmacokinetics of Therapeutic Monoclonal Antibodies, Clin Pharmacokinet, 49(10), 633-659, 2010.

European Medicines Agency, Guideline on the Clinical Investigation of the Pharmacokinetics of Therapeutic Proteins, European Medicines Agency, CHMP/EWP/89249/2004, 11 pages, 2007.

FDA, Review Memo—Keytruda, FDA, N/A, 19 pages, 2020.

Food and Drug Administration, FDA approves new dosing regimen for pembrolizumab, Food and Drug Administration, N/A, 2 pages, 2020.

Grimwood, Sarah et al., Target site occupancy: Emerging generalizations from clinical and preclinical studies, Pharmacology & Therapeutics, 122, 281-301, 2009.

Hamid, Omid et al., Randomized comparison of two doses of the anti-PD-1 monoclonal antibody MK-3475 for ipilimumab-refractory (IPIR) and IPI-naive (IPI-N) melanoma (MEL), Journal of Clinical Oncology, 32(Suppl15), Abstract 3000, 3 pages, 2014.

Hendrikx, Jeroen J.M.A. et al., Fixed Dosing of Monoclonal Antibodies in Oncology, the Oncologist, 22, 1212-1221, 2017.

Herbst, Roy S et al., Pembrolizumab versus docetaxel for previously treated, PD-L1-positive, advanced non-small-cell lung cancer (Keynote-010): a randomised controlled trial, Lancet, 387, 1540-1550, 2016.

Jiunn H. Lin, Pharmacokinetics of Biotech Drugs: Peptides, Proteins and Monoclonal Antibodies, Current Drug Metabolism, 10, 661-691, 2009.

Jones, Hannah M. et al., A Physiologically-Based Pharmacokinetic Model for the Prediction of Monoclonal Antibody Pharmacokinetics From In Vitro Data, CPT Pharmacometrics Syst. Pharmacol., 8, 738-747, 2019.

Keizer, Ron J. et al., Clinical Pharmacokinetics of Therapeutic Monoclonal Antibodies, Clin Pharmacokinet, 49(8), 493-507, 2010.

Kontermann, Roland, Strategies to Extend Plasma Half-Lives of Recombinant Antibodies, Biodrugs, 23(2), 93-109, 2009.

Koren, E. et al., Immune Responses to Therapeutic Proteins in Humans—Clinical Significance, Assessment and Prediction, Current Pharmaceutical Biotechnology, 3, 349-360, 2002.

Lee, Jean W et al., Bioanalysis of target biomarker and PK/PD relevancy during the development of biotherapeutics, Bioanalysis, 4(20), 2513-2523, 2012.

Li, Hongshan et al., Time dependent pharmacokinetics of pembrolizumab in patients with solid tumor and its correlation with best overall response, J Pharmacokinet Pharmacodyn, 44, 403-414, 2017.

Li, Tommy R. et al., Pivotal Dose of Pembrolizumab: A Dose-Finding Strategy for Immuno-Oncology, Clinical Pharmacology & Therapeutics, 110(1), 200-209, 2021.

Lindauer, A et al., Translational Pharmacokinetic/Pharmacodynamic Modeling of Tumor Growth Inhibition Supports Dose-Range Selection of the Anti-PD-1 Antibody Pembrolizumab, CPT Pharmacometrics Syst. Pharmacol., 6, 11-20, 2017.

Lobo, Evelyn D. et al., Antibody Pharmacokinetics and Pharmacodynamics, J Pharm Sci, 93(11), 2645-2668, 2004.

Lynch, Carmel M. et al., Practical considerations for nonclinical safety evaluation of therapeutic monoclonal antibodies, mAbs, 1:1, 2-11, 2009.

Marianne J. H. Van Vugt, et al., Immunogenicity of pembrolizumab in patients with advanced tumors, Journal for Immuno Therapy of Cancer, 7:212, 1-8, 2019.

Mould, D. R. et al., Basic Concepts in Population Modeling, Simulation, and Model-Based Drug Development, CPT: Pharmacometrics & Systems Pharmacology, 1:e6, 1-14, 2012.

Mould, Diane R et al., The pharmacokinetics and pharmacodynamics of monoclonal antibodies—mechanistic modeling applied to drug development, Current Opinion in Drug Discovery & Development, 10(1), 84-96, 2007.

Mould, DR et al., Basic Concepts in Population Modeling, Simulation, and Model-Based Drug Development—Part 2: Introduction to Pharmacokinetic Modeling Methods, CPT: Pharmacometrics & Systems Pharmacology, 2(e38), 1-14, 2013.

Newsome, Barrett W. et al., The clinical pharmacology of therapeutic monoclonal antibodies in the treatment of malignancy; have the magic bullets arrived?, Br J Clin Pharmacol, 66:1, 6-19, 2008.

Peletier, Lambertus A. et al., Dynamics of target-mediated drug disposition: characteristic profiles and parameter identification, J Pharmacokinet Pharmacodyn, 39, 429-451, 2012.

Putnam, Wendy S. et al., Pharmacokinetic, pharmacodynamic and immunogenicity comparability assessment strategies for monoclonal antibodies, Trends in Biotechnology, 28(10), 509-516, 2010.

(56) References Cited

OTHER PUBLICATIONS

Ribas, Antoni et al., Association of Pembrolizumab With Tumor Response and Survival Among Patients With Advanced Melanoma, JAMA, 315(15), 1600-1609, 2016.

Ribas, Antoni et al., Pembrolizumab versus investigator-choice chemotherapy for ipilimumab-refractory melanoma (Keynote-002): a randomised, controlled, phase 2 trial, Lancet Oncol, 16, 908-918, 2015.

Rippe, B. et al., Fluid and protein fluxes across small and large pores in the microvasculature. Application of two-pore equations, Acta Physiol Scand, 131, 411-428, 1987.

Sachs, Jeffrey R. et al., Optimal Dosing for Targeted Therapies in Oncology: Drug Development Cases Leading by Example, Clin Cancer Res, 22(6), 1318-1324, 2016.

Upton, RN et al., Basic Concepts in Population Modeling, Simulation, and Model-Based Drug Development: Part 3—Introduction to Pharmacodynamic Modeling Methods, CPT Pharmacometrics Syst. Pharmacol., 3(e88), 1-16, 2014.

US Dept of Health & Human Services Food & Drug Admin, Guidance for Industry-Exposure-Response Relationships—Study Design, Data Analysis, and Regulatory, US Dept of Health & Human Services Food & Drug Admin, N/A, 1-28, 2003.

Wang, Diane D. et al., Fixed Dosing Versus Body Size-Based Dosing of Monoclonal Antibodies in Adult Clinical Trials, Journal of Clinical Pharmacology, 49, 1012-1024, 2009.

Wang, W. et al., Monoclonal Antibody Pharmacokinetics and Pharmacodynamics, Nature, 84(5), 548-558, 2008.

Vugmeyster, Yulia et al., Biodistribution of [125I]-Labeled Therapeutic Proteins: Application in Protein Drug Development Beyond Oncology, J Pharm Sci, 99(2), 1028-1045, 2010.

Zhu, Hui et al., Tumor Pretargeting for Radioimmunodetection and Radioimmunotherapy, J Nucl Med, 39, 65-76, 1998.

Dang, et al., "Pembrolizumab for the treatment of PD-L1 positive advanced or metastatic non-small cell lung cancer", Expert Rev Anticancer Ther., vol. 16(1), pp. 13-20, 2016.

Ernstoff, Marc S., "The clinical pharmacology of therapeutic monoclonal antibodies in the treatment of malignancy; have the magic bullets arrived?", British Journal of Clinical Pharmacology, vol. 6:1, pp. 6-19, May 22, 2008.

Food and Drug Administration, Guidance for Industry Population Pharmacokinetics, CP 1, N/A, 35 pages, 1999.

Glassman, Patrick M., et al., "Physiologically-based modeling to predict the clinical behavior of monoclonal antibodies directed against lymphocyte antigens", MABS, vol. 9:2, pp. 297-306, 2017.

Hansel, Trevor T., et al., "The safety and side effects of monoclonal antibodies", Nature Reviews Drug Discovery, vol. 9, pp. 325-338, Apr. 2010.

Jain, Rajul K. et al., "Phase I Oncology Studies: Evidence That in the Era of Targeted Therapies Patients on Lower Doses Do Not Fare Worse", American Association for Cancer Research., vol. 16(4), pp. 1289-1297, 2010.

Mathijssen, Ron H. J., et al., "Determining the optimal dose in the development of anticancer agents", Nature Reviews Clinical Oncology, vol. 11, pp. 272-281, May 2014.

Nghiem, Paul T., et al., "PD-1 blockade with pembrolizumab in advanced Merkel-cell carcinoma", N Engl J Med, 374;26, 2542-2552, 2016.

Ryman, Josiah T., et al., "Pharmacokinetics of Monoclonal Antibodies", CPT Pharmacometrics Syst. Pharmacol., vol. 6, pp. 576-588, 2017.

Tosi, Diego, et al., "Clinical Development Strategies and Outcomes in First-in-Human Trials of Monoclonal Antibodies", American Society of Clinical Oncology, vol. 33, pp. 2158-2165, 2015.

Truong, Phu et al., Metastatic Hepatocellular Carcinoma Responsive to Pembrolizumab, Cureus, 8(6): e631, 1-3, 2016.

Wong, et al, "Dose-limiting toxicity and maximum tolerated dose: still fit for purpose?", thelancet.com, vol. 16, pp. 1287-1288, Oct. 2015.

Zinzani, Pier Luigi et al., Safety and tolerability of pembrolizumab in patients with relapsed/refractory primary mediastinal large B-cell lymphoma, Blood, 130(3), 267-270, 2017.

Bates, Adam et al., David vs. Goliath: The Structure, Function, and Clinical Prospects of Antibody Fragments, Antibodies, 8(2), 1-31, 2019.

Freshwater et al., Evaluation of dosing strategy for pembrolizumab for oncology indications, Journal for ImmunoTherapy of Cancer, vol. 5, Article No. 43 (2017).†

\* cited by examiner
† cited by third party

Pembrolizumab Light Chain

EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:5).

Pembrolizumab Heavy Chain

QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO:10),

FIG.1

SEQUENCE LISTING

```
<160> NUMBER OF SEQ ID NOS: 25

<210> SEQ ID NO 1
<211> LENGTH: 15
<212> TYPE: PRT
<213> ORGANISM: Artificial Sequence
<220> FEATURE:
<223> OTHER INFORMATION: Pembrolizumab- Light chain CDR1

<400> SEQUENCE: 1

Arg Ala Ser Lys Gly Val Ser Thr Ser Gly Tyr Ser Tyr Leu His
1               5                   10                  15

<210> SEQ ID NO 2
<211> LENGTH: 7
<212> TYPE: PRT
<213> ORGANISM: Artificial Sequence
<220> FEATURE:
```

<223> OTHER INFORMATION: Pembrolizumab-Light chain CDR2

<400> SEQUENCE: 2

Leu Ala Ser Tyr Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Pembrolizumab-Light chain CDR3

<400> SEQUENCE: 3

Gln His Ser Arg Asp Leu Pro Leu Thr
1               5

<210> SEQ ID NO 4
<211> LENGTH: 111
<212> TYPE: PRT
<213> ORGANISM: Artificial Sequence
<220> FEATURE:
<223> OTHER INFORMATION: Pembrolizumab-Light chain variable region

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 5
<211> LENGTH: 218
<212> TYPE: PRT
<213> ORGANISM: Artificial Sequence
<220> FEATURE:
<223> OTHER INFORMATION: Pembrolizumab-Light chain

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

```
Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 6
<211> LENGTH: 5
<212> TYPE: PRT
<213> ORGANISM: Artificial Sequence
<220> FEATURE:
<223> OTHER INFORMATION: Pembrolizumab-Heavy chain CDR1

<400> SEQUENCE: 6

Asn Tyr Tyr Met Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Pembrolizumab-Heavy chain CDR2

<400> SEQUENCE: 7

Gly Ile Asn Pro Ser Asn Gly Gly Thr Asn Phe Asn Glu Lys Phe Lys
1               5                   10                  15

Asn

<210> SEQ ID NO 8
<211> LENGTH: 11
<212> TYPE: PRT
<213> ORGANISM: Artificial Sequence
<220> FEATURE:
<223> OTHER INFORMATION: Pembrolizumab-Heavy chain CDR3

<400> SEQUENCE: 8

Arg Asp Tyr Arg Phe Asp Met Gly Phe Asp Tyr
1               5                   10

<210> SEQ ID NO 9
<211> LENGTH: 120
<212> TYPE: PRT
<213> ORGANISM: Artificial Sequence
<220> FEATURE:
<223> OTHER INFORMATION: Pembrolizumab-Heavy chain variable region

<400> SEQUENCE: 9

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
```

```
                    20                  25                  30
Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
            115                 120

<210> SEQ ID NO 10
<211> LENGTH: 447
<212> TYPE: PRT
<213> ORGANISM: Artificial Sequence
<220> FEATURE:
<223> OTHER INFORMATION: Pembrolizumab- Heavy chain

<400> SEQUENCE: 10

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
                    260                 265                 270
Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 11
<211> LENGTH: 15
<212> TYPE: PRT
<213> ORGANISM: Artificial Sequence
<220> FEATURE:
<223> OTHER INFORMATION: hPD-1.08A Light Chain CDR1

<400> SEQUENCE: 11

Arg Ala Ser Lys Ser Val Ser Thr Ser Gly Phe Ser Tyr Leu His
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: hPD-1.08A Light Chain CDR2

<400> SEQUENCE: 12

Leu Ala Ser Asn Leu Glu Ser
1               5

<210> SEQ ID NO 13
<211> LENGTH: 9
<212> TYPE: PRT
<213> ORGANISM: Artificial Sequence
<220> FEATURE:
<223> OTHER INFORMATION: hPD-1.08A Light Chain CDR3

<400> SEQUENCE: 13

Gln His Ser Trp Glu Leu Pro Leu Thr
1               5

<210> SEQ ID NO 14
<211> LENGTH: 5
<212> TYPE: PRT
<213> ORGANISM: Artificial Sequence
```

```
<220> FEATURE:
<223> OTHER INFORMATION: hPD-1.08A Heavy Chain CDR1

<400> SEQUENCE: 14

Ser Tyr Tyr Leu Tyr
1               5

<210> SEQ ID NO 15
<211> LENGTH: 17
<212> TYPE: PRT
<213> ORGANISM: Artificial Sequence
<220> FEATURE:
<223> OTHER INFORMATION: hPD-1.08A Heavy Chain CDR2

<400> SEQUENCE: 15

Gly Val Asn Pro Ser Asn Gly Gly Thr Asn Phe Ser Glu Lys Phe Lys
1               5                   10                  15

Ser

<210> SEQ ID NO 16
<211> LENGTH: 11
<212> TYPE: PRT
<213> ORGANISM: Artificial Sequence
<220> FEATURE:
<223> OTHER INFORMATION: hPD-1.08A Heavy Chain CDR3

<400> SEQUENCE: 16

Arg Asp Ser Asn Tyr Asp Gly Gly Phe Asp Tyr
1               5                   10

<210> SEQ ID NO 17
<211> LENGTH: 290
<212> TYPE: PRT
<213> ORGANISM: Homo sapiens

<400> SEQUENCE: 17

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190
```

```
Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Gly Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 18
<211> LENGTH: 112
<212> TYPE: PRT
<213> ORGANISM: Artificial Sequence
<220> FEATURE:
<223> OTHER INFORMATION: 20C3 Light Chain Mature Variable Region

<400> SEQUENCE: 18

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asp Val Val Thr Phe Gly Ala Gly Thr Lys Leu Glu Leu Lys
            100                 105                 110

<210> SEQ ID NO 19
<211> LENGTH: 122
<212> TYPE: PRT
<213> ORGANISM: Artificial Sequence
<220> FEATURE:
<223> OTHER INFORMATION: 20C3 Heavy Chain Mature Variable Region

<400> SEQUENCE: 19

Gln Val Gln Val Gln Gln Ser Gly Ala Glu Leu Ala Glu Pro Gly Ala
1               5                   10                  15

Ser Val Lys Met Ser Cys Lys Ala Ser Gly Tyr Ile Phe Thr Ser Tyr
            20                  25                  30

Trp Met His Trp Leu Lys Gln Arg Pro Gly Gln Gly Leu Glu Trp Ile
        35                  40                  45

Gly Tyr Ile Asn Pro Ser Ser Asp Tyr Asn Glu Tyr Ser Glu Lys Phe
    50                  55                  60

Met Asp Lys Ala Thr Leu Thr Ala Asp Lys Ala Ser Thr Thr Ala Tyr
65                  70                  75                  80

Met Gln Leu Ile Ser Leu Thr Ser Glu Asp Ser Ala Val Tyr Tyr Cys
```

```
                    85                  90                  95
Ala Arg Ser Gly Trp Leu Val His Gly Asp Tyr Tyr Phe Asp Tyr Trp
                100                 105                 110
Gly Gln Gly Thr Thr Leu Thr Val Ser Ser
        115                 120

<210> SEQ ID NO 20
<211> LENGTH: 112
<212> TYPE: PRT
<213> ORGANISM: Artificial Sequence
<220> FEATURE:
<223> OTHER INFORMATION: 22C3 Light Chain Mature Variable Region

<400> SEQUENCE: 20

Asp Ile Val Met Ser Gln Ser Pro Ser Ser Leu Ala Val Ser Ala Gly
1               5                   10                  15
Glu Lys Val Thr Met Thr Cys Lys Ser Ser Gln Ser Leu Leu His Thr
                20                  25                  30
Ser Thr Arg Lys Asn Tyr Leu Ala Trp Tyr Gln Gln Lys Pro Gly Gln
            35                  40                  45
Ser Pro Lys Leu Leu Ile Tyr Trp Ala Ser Thr Arg Glu Ser Gly Val
        50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Lys Gln
                85                  90                  95
Ser Tyr Asp Val Val Thr Phe Gly Ala Gly Thr Lys Leu Glu Leu Lys
                100                 105                 110

<210> SEQ ID NO 21
<211> LENGTH: 122
<212> TYPE: PRT
<213> ORGANISM: Artificial Sequence
<220> FEATURE:
<223> OTHER INFORMATION: 22C3 Heavy Chain Mature Variable Region

<400> SEQUENCE: 21

Gln Val His Leu Gln Gln Ser Gly Ala Glu Leu Ala Lys Pro Gly Ala
1               5                   10                  15
Ser Val Lys Met Ser Cys Lys Ala Ser Gly Tyr Thr Phe Thr Ser Tyr
                20                  25                  30
Trp Ile His Trp Ile Lys Gln Arg Pro Gly Gln Gly Leu Glu Trp Ile
            35                  40                  45
Gly Tyr Ile Asn Pro Ser Ser Gly Tyr His Glu Tyr Asn Gln Lys Phe
        50                  55                  60
Ile Asp Lys Ala Thr Leu Thr Ala Asp Arg Ser Ser Ser Thr Ala Tyr
65                  70                  75                  80
Met His Leu Thr Ser Leu Thr Ser Glu Asp Ser Ala Val Tyr Tyr Cys
                85                  90                  95
Ala Arg Ser Gly Trp Leu Ile His Gly Asp Tyr Tyr Phe Asp Phe Trp
                100                 105                 110
Gly Gln Gly Thr Thr Leu Thr Val Ser Ser
        115                 120

<210> SEQ ID NO 22
<211> LENGTH: 111
<212> TYPE: PRT
<213> ORGANISM: Artificial Sequence
<220> FEATURE:
```

<223> OTHER INFORMATION: K09A-L-16 light chain variable region

<400> SEQUENCE: 22

```
Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110
```

<210> SEQ ID NO 23
<211> LENGTH: 111
<212> TYPE: PRT
<213> ORGANISM: Artificial Sequence
<220> FEATURE:
<223> OTHER INFORMATION: K09A-L-17 light chain variable region

<400> SEQUENCE: 23

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys
            100                 105                 110
```

<210> SEQ ID NO 24
<211> LENGTH: 218
<212> TYPE: PRT
<213> ORGANISM: Artificial Sequence
<220> FEATURE:
<223> OTHER INFORMATION: K09A-L-16 light chain full length

<400> SEQUENCE: 24

```
Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
```

```
                 65                  70                  75                  80
Arg Val Glu Ala Glu Asp Val Gly Val Tyr Tyr Cys Gln His Ser Arg
                     85                  90                  95

Asp Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 25
<211> LENGTH: 218
<212> TYPE: PRT
<213> ORGANISM: Artificial Sequence
<220> FEATURE:
<223> OTHER INFORMATION: K09A-L-17 light chain full length

<400> SEQUENCE: 25

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
                20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
        50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
        195             200             205

Val Thr Lys Ser Phe Asn Arg Gly Glu Cys
        210             215
```

METHODS FOR TREATING CANCER WITH ANTI-PD-1 ANTIBODIES

CROSS-REFERENCE TO RELATED APPLICATIONS

This application is a § 371 National Phase Application of International Application No. PCT/US2019/017177, filed Feb. 8, 2019, which claims the benefit of U.S. provisional application No. 62/630,038, filed Feb. 13, 2018, and U.S. provisional application No. 62/732,828, filed Sep. 18, 2018, the contents of which are hereby incorporated by reference in their entirety.

FIELD OF THE INVENTION

The present invention relates to therapies useful for the treatment of cancer. In particular, the invention relates to a method for treating cancer which comprises administering to a patient in need thereof an anti-PD-1 antibody, or antigen binding fragment thereof, using the dosage regimens specified herein.

REFERENCE TO SEQUENCE LISTING SUBMITTED ELECTRONICALLY

The sequence listing of the present application is submitted electronically via EFS-Web as an ASCII formatted sequence listing with a file name "24567WOPCT-SEQLIST-25JAN2019.TXT", creation date of Jan. 25, 2019, and a size of 23.7 kb. This sequence listing submitted via EFS-Web is part of the specification and is herein incorporated by reference in its entirety.

BACKGROUND OF THE INVENTION

PD-1 is recognized as an important player in immune regulation and the maintenance of peripheral tolerance. PD-1 is moderately expressed on naive T, B and NKT cells 25 and up-regulated by T/B cell receptor signaling on lymphocytes, monocytes and myeloid cells (Sharpe et al., The function of programmed cell death 1 and its ligands in regulating autoimmunity and infection. *Nature Immunology* (2007); 8:239-245).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (Dong et al., *Nat Med.* 8(8):793-800 (2002); Yang et al. *Invest Ophthalmol Vis Sci.* 49: 2518-2525 (2008); Ghebeh et al. *Neoplasia* 8:190-198 (2006); Hamanishi et al., *Proc. Natl. Acad. Sci. USA* 104: 3360-3365 (2007); Thompson et al., *Cancer* 5: 206-211 (2006); Nomi et al., *Clin. Cancer Research* 13:2151-2157 (2007); Ohigashi et al., *Clin. Cancer Research* 11: 2947-2953 (2005); Inman et al., *Cancer* 109: 1499-1505 (2007); Shimauchi et al. *Int. J. Cancer* 121:2585-2590 (2007); Gao et al. *Clin. Cancer Research* 15: 971-979 (2009); Nakanishi J. *Cancer Immunol Immunother.* 56: 1173-1182 (2007); and Hino et al., *Cancer* 00: 1-9 (2010)).

Similarly, PD-1 expression on tumor infiltrating lymphocytes was found to mark dysfunctional T cells in breast cancer and melanoma (Ghebeh et al, *BMC Cancer.* 2008 8:5714-15 (2008); Ahmadzadeh et al., *Blood* 114: 1537-1544 (2009)) and to correlate with poor prognosis in renal cancer (Thompson et al., *Clinical Cancer Research* 15: 1757-1761(2007)). Thus, it has been proposed that PD-L1 expressing tumor cells interact with PD-1 expressing T cells to attenuate T cell activation and evasion of immune surveillance, thereby contributing to an impaired immune response against the tumor.

Immune checkpoint therapies targeting the PD-1 axis have resulted in groundbreaking improvements in clinical response in multiple human cancers (Brahmer et al., *N Engl J Med* 2012, 366: 2455-65; Garon et al. *N Engl J Med* 2015, 372: 2018-28; Hamid et al., *N Engl J Med* 2013, 369: 134-44; Robert et al., *Lancet* 2014, 384: 1109-17; Robert et al., *N Engl J Med* 2015, 372: 2521-32; Robert et al., *N Engl J Med* 2015, 372: 320-30; Topalian et al., *N Engl J Med* 2012, 366: 2443-54; Topalian et al., *J Clin Oncol* 2014, 32: 1020-30; Wolchok et al., *N Engl J Med* 2013, 369: 122-33). Immune therapies targeting the PD-1 axis include monoclonal antibodies directed to the PD-1 receptor (KEYTRUDA™ (pembrolizumab), Merck and Co., Inc., Kenilworth, N.J., USA and OPDIVO™ (nivolumab), Bristol-Myers Squibb Company, Princeton, N.J., USA) and also those that bind to the PD-L1 ligand (MPDL3280A; TECENTRIQ™ (atezolizumab), Genentech, San Francisco, Calif., USA; IMFINZI™ (durvalumab), AstraZeneca Pharmaceuticals LP, Wilmington, Del.; BAVENCIO™ (avelumab), Merck KGaA, Darmstadt, Germany). Both therapeutic approaches have demonstrated anti-tumor effects in numerous cancer types.

It would be beneficial to develop additional dosing schedules that allow for the administration of a safe and effective dose of an anti-PD-1 antibody that is more convenient for patients.

SUMMARY OF THE INVENTION

The present invention provides alternative, less frequent, dosing regimens for treating a cancer patient with an anti-PD-1 antibody, or antigen-binding fragment thereof, wherein the dosing schedule is expected to provide a safe and effective dose of the anti-PD-1 antibody, or antigen-binding fragment thereof. Specifically, the invention provides a method of treating cancer in a human patient comprising administering about 400 mg of an anti-PD-1 antibody or antigen binding fragment thereof to the patient every six weeks, wherein the anti-PD-1 antibody or antigen-binding fragment thereof comprises (a) light chain complementarity determining regions (CDRs) comprising a sequence of amino acids as set forth in SEQ ID NOs: 1, 2 and 3 and heavy chain CDRs comprising a sequence of amino acids as set forth in SEQ ID NOs: 6, 7 and 8; or (b) light chain CDRs comprising a sequence of amino acids as set forth in SEQ ID NOs: 11, 12 and 13 and heavy chain CDRs comprising a sequence of amino acids as set forth in SEQ ID NOs: 14, 15 and 16. In preferred embodiments of the invention, the antibody or antigen-binding fragment is pembrolizumab.

In embodiments of the invention, the amount of anti-PD-1 antibody or antigen-binding fragment thereof administered to the patient is from about 350 mg to about 450 mg. In further embodiments, the amount of antibody or antigen-binding fragment is about 400 mg. In further embodiments, the amount of antibody or antigen-binding fragment is 400 mg.

In all of the above treatment methods, compositions and uses herein, the PD-1 antibody or antigen-binding fragment inhibits the binding of PD-L1 to PD-1, and preferably also inhibits the binding of PD-L2 to PD-1. In some preferred embodiments of the treatment methods, compositions and uses of the invention, the PD-1 antibody or antigen-binding fragment is a monoclonal antibody, which specifically binds to PD-1 and blocks the binding of PD-L1 to PD-1. In one particular embodiment, the anti-PD-1 antibody comprises a heavy chain and a light chain, and wherein the heavy and light chains comprise the amino acid sequences shown in FIG. 1 (SEQ ID NO:5 and SEQ ID NO:10).

In some embodiments of any of the above treatment methods, compositions and uses, the cancer expresses one or both of PD-L1 and PD-L2. In some embodiments, PD-L1 expression is elevated in the cancer.

In certain embodiments of any of the methods described herein, the anti-PD-1 antibody or antigen binding fragment is administered to a patient subcutaneously.

In alternative embodiments of any of the methods described herein, the anti-PD-1 antibody or antigen binding fragment is administered to a patient intravenously.

BRIEF DESCRIPTION OF THE DRAWINGS

FIG. 1 shows amino acid sequences of the light chain and heavy chain for an exemplary anti-PD-1 monoclonal antibody useful in the present invention (SEQ ID NOs:5 and 10, respectively). Light chain and heavy chain variable regions are underlined (SEQ ID NO's 4 and 9) and CDRs are bold and boxed.

DETAILED DESCRIPTION OF THE INVENTION

I. Definitions and Abbreviations

Figure 2:
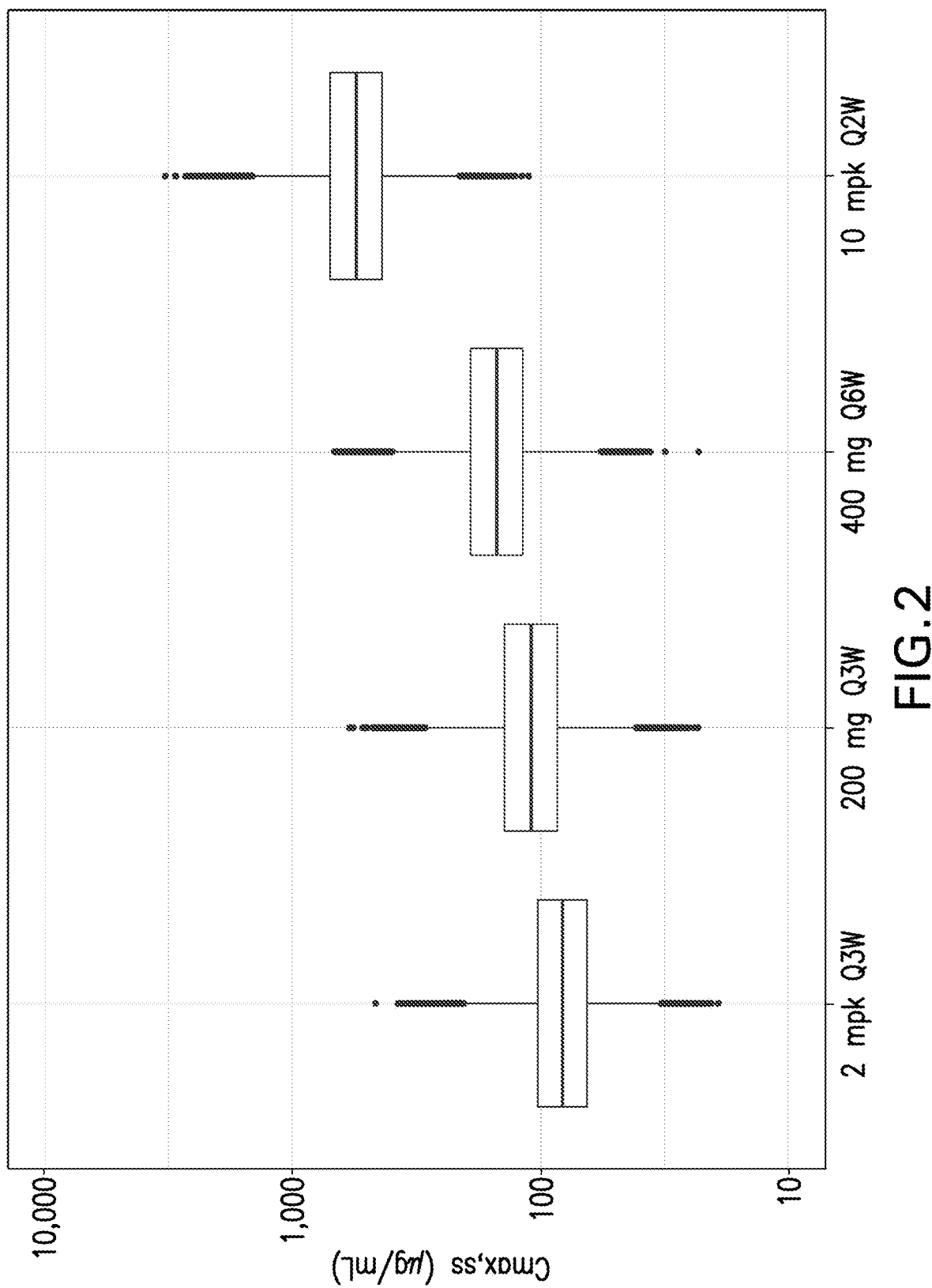
FIG. 2 shows that pembrolizumab Cmax at steady state for 400 mg Q6W lies within the range from 2 mg/kg Q3W and 200 mg Q3W to 10 mg/kg Q2W.

As used throughout the specification and appended claims, the following abbreviations apply:
E adverse event
AUCss area under the concentration-time curve at steady state
BICR blinded independent central review
Cavg,ss time averaged concentration at steady state
CDR complementarity determining region
CI confidence interval
Cmax,ss peak concentrations at steady state
Cmin,ss trough concentrations at steady state
CPS combined positive score
DOR duration of response
ECG electrocardiogram
ECOG Eastern Cooperative Oncology Group
E-R exposure (concentration)-response
FFPE formalin-fixed paraffin-embedded
FR framework region
GM geometric mean
HCC hepatocellular carcinoma
HNSCC head and neck squamous cell cancer
HL Hodgkin lymphoma
IgG immunoglobulin G
IHC immunohistochemistry or immunohistochemical
IV intravenous
LPS lymphoma proportion score
mAb monoclonal antibody
MCC Merkel cell carcinoma
MEL melanoma
MMR mismatch repair
MPS modified proportion score
MRI magnetic resonance imaging
MSI-H microsatellite instability-high
NCI CTCAE National Cancer Institute—Common Terminology Criteria for Adverse Events
NSCLC non-small cell lung cancer
ORR objective response rate
OS overall survival
PD progressive disease
PD-1 programmed death 1 (a.k.a. programmed cell death-1 and programmed death receptor 1)
PD-L1 programmed cell death 1 ligand 1
PD-L2 programmed cell death 1 ligand 2
PFS progression free survival
PK pharmacokinetic
Q2W one dose every two weeks
Q3W one dose every three weeks
Q6W one dose every six weeks
RCC renal cell carcinoma
SAE serious adverse event
SC subcutaneous
TPS tumor proportion score
$V_H$ immunoglobulin heavy chain variable region
$V_L$ immunoglobulin light chain variable region So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

Reference to "or" indicates either or both possibilities unless the context clearly dictates one of the indicated possibilities. In some cases, "and/or" was employed to highlight either or both possibilities.

As used herein, including the appended claims, the singular forms of words such as "a," "an," and "the," include their corresponding plural references unless the context clearly dictates otherwise.

The term "about", when modifying the quantity (e.g., mg) of a substance or composition, or the value of a parameter characterizing a step in a method, or the like, refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1%, ±0.5%, ±1%, ±2%, ±3%, ±4%, ±5%, ±6%, ±7%, 8%, ±9% or 10%. When referring to the dosage of "about 400 mg," the dosage can be from 360 mg to 440 mg, from 370 mg to 430 mg, from 380 mg to 420 mg, from 390 mg to 410 mg, from 395 mg to 405 mg, from 400 mg to 440 mg, or from 390 mg to 440 mg. It alternative embodiments, the dosage can be 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, or 440 mg. When referring to the amount of time between administrations in a therapeutic treatment regimen (i.e., amount of time between administrations of the anti-PD-1 antibody or antigen binding fragment thereof, e.g. "about 6 weeks," which is used interchangeably herein with "approximately every six weeks"), "about" refers to the stated time a variation that can occur due to patient/clinician scheduling and availability around the 6-week target date. For example, "about 6 weeks" can refer to 6 weeks 5 days, 6 weeks 4 days, 6 weeks 3 days, 6 weeks 2 days or 6 weeks 1 day, or may refer to 5 weeks, 2 days through 6 weeks, 5 days.

Pharmacokinetic "steady state" is a period of time during which any accumulation of drug concentrations owing to multiple doses has been maximized and systemic drug exposure is considered uniform after each subsequent dose administered; in the specific case of pembrolizumab, steady state is achieved at and after ~16 weeks of administration.

AUCss, Cavg,ss and Cmin,ss are pharmacokinetic measures of the systemic exposure to the drug (e.g. pembrolizumab) in humans after its administration, and are typically considered drivers of drug efficacy. AUCss and Cavg,ss represent the average exposure over a dosing interval, but differ in terms of units. "Cmin,ss" represents the minimum or lowest (trough) drug concentration observed at the end of a dosing interval, just before the next dose is administered.

"Cmax,ss" is the maximum or highest (peak) drug concentration observed soon after its administration. In the specific case of pembrolizumab, which is administered as intravenous infusion, the peak concentration occurs immediately after end of infusion. Cmax,ss is a metric that is typically considered a driver of driver safety.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Treat" or "treating" a cancer, as used herein, means to administer an anti-PD-1 antibody, or antigen-binding fragment, to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. "Treatment" may include one or more of the following: inducing/increasing an antitumor immune response, decreasing the number of one or more tumor markers, halting or delaying the growth of a tumor or blood cancer or progression of disease associated with PD-1 binding to its ligands PD-L1 and/or PD-L2 ("PD-1-related disease") such as cancer, stabilization of PD-1-related disease, inhibiting the growth or survival of tumor cells, eliminating or reducing the size of one or more cancerous lesions or tumors, decreasing the level of one or more tumor markers, ameliorating or abrogating the clinical manifestations of PD-1-related disease, reducing the severity or duration of the clinical symptoms of PD-1-related disease such as cancer, prolonging the survival of a patient relative to the expected survival in a similar untreated patient, and inducing complete or partial remission of a cancerous condition or other PD-1 related disease.

Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a therapeutically effective amount is any of progression free survival (PFS), disease free survival (DFS) or overall survival (OS). PFS, also referred to as "Time to Tumor Progression" indicates the length of time during and after treatment that the cancer does not grow, and includes the amount of time patients have experienced a complete response or a partial response, as well as the amount of time patients have experienced stable disease. DFS refers to the length of time during and after treatment that the patient remains free of disease. OS refers to a prolongation in life expectancy as compared to naive or untreated individuals or patients. While an embodiment of the treatment methods, compositions and uses of the present invention may not be effective in achieving a positive therapeutic effect in every patient, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The term "patient" (alternatively referred to as "subject" or "individual" herein) refers to a mammal (e.g., rat, mouse, dog, cat, rabbit) capable of being treated with the methods and compositions of the invention, most preferably a human. In some embodiments, the patient is an adult patient. In other embodiments, the patient is a pediatric patient.

The term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, humanized, fully human antibodies, and chimeric antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) *Adv. Prot. Chem.* 32:1-75; Kabat, et al., (1977) *J. Biol. Chem.* 252: 6609-6616; Chothia, et al., (1987) *J Mol. Biol.* 196:901-917 or Chothia, et al., (1989) *Nature* 342:878-883.

The term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). The term "framework" or "FR" residues refers to those variable domain residues other than the hypervariable region residues defined herein as CDR residues.

Unless otherwise indicated, an "antibody fragment" or "antigen binding fragment" refers to antigen binding fragments of antibodies, i.e. antibody fragments that retain the ability to specifically bind to the antigen bound by the full-length antibody, e.g. fragments that retain one or more CDR regions. Examples of antibody binding fragments include, but are not limited to, Fab, Fab', F(ab')$_2$, and Fv fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include, but are not limited to, squamous cell carcinoma, myeloma, small-cell lung cancer, non-small cell lung cancer, glioma, Hodgkin lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Additional cancers that may be treated in accordance with the present invention include those characterized by elevated expression of one or both of PD-L1 and PD-L2 in tested tissue samples.

"Biotherapeutic agent" means a biological molecule, such as an antibody or fusion protein, that blocks ligand/receptor signaling in any biological pathway that supports tumor maintenance and/or growth or suppresses the anti-tumor immune response.

"CDR" or "CDRs" means complementarity determining region(s) in an immunoglobulin variable region, generally defined using the Kabat numbering system.

"Platinum-containing chemotherapy" (also known as platins) refers to the use of chemotherapeutic agent(s) used to treat cancer that are coordination complexes of platinum. Platinum-containing chemotherapeutic agents are alkylating agents that crosslink DNA, resulting in ineffective DNA mismatch repair and generally leading to apoptosis. Examples of platins include cisplatin, carboplatin, and oxaliplatin.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytotoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Chothia" means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in the art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antigen binding fragment that consists essentially of a recited amino acid sequence may also include one or more amino acids, including substitutions of one or more amino acid residues, which do not materially affect the properties of the binding compound.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Diagnostic anti-PD-L monoclonal antibody" means a mAb which specifically binds to the mature form of the designated PD-L (PD-L1 or PD-L2) that is expressed on the surface of certain mammalian cells. A mature PD-L lacks the presecretory leader sequence, also referred to as leader peptide The terms "PD-L" and "mature PD-L" are used interchangeably herein, and shall be understood to mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 of the following sequence:

```
                                         (SEQ ID NO: 17)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.
```

Specific examples of diagnostic anti-human PD-L1 mAbs useful as diagnostic mAbs for immunohistochemistry (TIC) detection of PD-L1 expression in formalin-fixed, paraffin-embedded (FFPE) tumor tissue sections are antibody 20C3 and antibody 22C3, which are described in WO2014/100079. These antibodies comprise the light chain and heavy chain variable region amino acid sequences shown in Table 2 below:

TABLE 2

Monoclonal Antibodies 20C3 and 22C3

20C3 Light Chain Mature Variable Region

```
DIVMSQSPSSLAVSAGEKVTMSCKSSQSLLNSRTRKNYLAWYQQ    SEQ ID
KPGQSPKWYWASTRESGVPDRFTGSGSGTDFTLTISSVQAEDLA    NO: 18
VYYCQQSYDVVTFGAGTKLELK
```

20C3 Heavy Chain Mature Variable Region

```
QVQVQQSGAELAEPGASVKMSCKASGYIFTSYWMHWLKQRPGQ     SEQ ID
GLEWIGYINPSSDYNEYSEKFMDKATLTADKASTTAYMQLISL     NO: 19
TSEDSAVYYCARSGWLVHGDYYFDYWGQGTTLTVSS
```

22C3 Light Chain Mature Variable Region

```
DIVMSQSPSSLAVSAGEKVTMTCKSSQSLLHTSTRKNYLAWYQQ    SEQ ID
KPGQSPKWYWASTRESGVPDRFTGSGSGTDFTLTISSVQAEDLA    NO: 20
VYYCKQSYDVVTFGAGTKLELK
```

22C3 Heavy Chain Mature Variable Region

```
QVHLQQSGAELAKPGASVKMSCKASGYTFTSYWIHWIKQRPGQG    SEQ ID
LEWIGYINPSSGYHEYNQKFIDKATLTADRSSSTAYMHLTSLTS    NO: 21
EDSAVYYCARSGWLIHGDYYFDFWGQGTTLTVSS
```

Another anti-human PD-L1 mAb that has been reported to be useful for IC detection of PD-L1 expression in FFPE tissue sections (Chen, B. J. et al., *Cin Cancer Res* 19: 3462-3473 (2013)) is a rabbit anti-human PD-L1 mAb publicly available from Sino Biological, Inc. (Beijing, P. R. China; Catalog number 10084-R15).

"Framework region" or "FR" as used herein means the immunoglobulin variable regions excluding the CDR regions.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat," as used herein, means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975)*Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

An "anti-PD-1 antibody" useful in the any of the treatment methods, compositions and uses of the present invention include monoclonal antibodies (mAb), or antigen binding fragments thereof, which specifically bind to human PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment methods, compositions and uses of the present invention in which a human individual is being treated, the PD-1 antibody or antigen binding fragment thereof is a PD-1 antagonist that blocks binding of human PD-L1 to human PD-1, or blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively. An anti-PD-1 antibody may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

"PD-L1" or "PD-L2" expression means any detectable level of expression of the designated PD-L protein on the cell surface or of the designated PD-L mRNA within a cell or tissue, unless otherwise defined. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and real-time quantitative RT-PCR.

Several approaches have been described for quantifying PD-L1 protein expression in IHC assays of tumor tissue sections. See, e.g., Thompson et al., *PNAS* 101 (49): 17174-17179 (2004); Thompson et al., *Cancer Res.* 66:3381-3385 (2006); Gadiot et al., *Cancer* 117:2192-2201 (2011); Taube et al., *Sci Transl Med* 4, 127ra37 (2012); and Toplian et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

A tissue section from a tumor that has been stained by IHC with a diagnostic PD-L1 antibody may also be scored for PD-L1 protein expression by assessing PD-L1 expression in both the tumor cells and infiltrating immune cells in the tissue section using a scoring process. See WO 2014/165422. One PD-L1 scoring process comprises examining each tumor nest in the tissue section for staining, and assigning to the tissue section one or both of a modified H score (MHS) and a modified proportion score (MPS). To assign the MS, four separate percentages are estimated across all of the viable tumor cells and stained mononuclear inflammatory cells in all of the examined tumor nests: (a) cells that have no staining (intensity=0), (b) weak staining (intensity=1+), (c) moderate staining (intensity=2+) and (d) strong staining (intensity=3+). A cell must have at least partial membrane staining to be included in the weak, moderate or strong staining percentages. The estimated percentages, the sum of which is 100%, are then input into the formula of 1×(percent of weak staining cells)+2×(percent of moderate staining cells)+3×(percent of strong staining cells), and the result is assigned to the tissue section as the MHS. The MPS is assigned by estimating, across all of the viable tumor cells and stained mononuclear inflammatory cells in all of the examined tumor nests, the percentage of cells that have at least partial membrane staining of any intensity, and the resulting percentage is assigned to the tissue section as the MPS. In some embodiments, the tumor is designated as positive for PD-L1 expression if the NHS or the MPS is positive.

Another method for scoring/quantifying PD-L1 expression in a tumor is the "combined positive score" or "CPS," which refers to an algorithm for determining a PD-L1 expression score from a tumor sample of a patient. The CPS is useful in selecting patients for treatment with particular treatment regimens including methods of treatment comprising administration of an anti-PD-1 antibody in which expression of PD-L1 is associated with a higher response rate in a particular patient population relative to same patient population that does not express PD-L1. The CPS is determined by determining the number of viable PD-L1 positive tumor cells, the number of viable PD-L1 negative tumor cells, and the number of viable PD-L1 positive mononuclear inflammatory cells (MIC) in a tumor tissue from a patient having a tumor and calculating the CPS using the following formula:

$$\frac{(\# \; Pd\text{-}L1 \; \text{positive tumor cells}) + (\# \; Pd\text{-}L1 \; \text{positive } MIC)}{(\# \; Pd\text{-}L1 \; \text{positive tumor cells}) + (Pd\text{-}L1 \; \text{negative tumor cells})} \times 100\%$$

In particular embodiments, the PD-L1 expression scoring method used is the "lymphoma proportion score." Lymphoma is characterized by a homogeneous population of confluent cells which efface the architecture of the lymph node or the architecture of metastatic site. The "LPS" or "lymphoma proportion score" is the percentage of this population of cells which express PD-L1. When determining the LPS, no attempt is made to distinguish the truly neoplastic cells from the reactive cells. PD-L1 expression is characterized by partial or complete membrane staining at any intensity.

Yet another scoring method for PD-L1 expression is the "TPS" or "tumor proportion score," which is the percentage of tumor cells expressing PD-L1 on the cell membrane. TPS typically includes the percentage of neoplastic cells expressing PD-L1 at any intensity (weak, moderate, or strong), which can be determining using an immunohistochemical assay using a diagnostic anti-human PD-L1 mAb, e.g. antibody 20C3 and antibody 22C3, described, supra. Cells are considered to express PD-L1 if membrane staining is present, including cells with partial membrane staining.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, or 30% greater than in the control.

"Tissue section" refers to a single part or piece of a tissue sample, e.g., a thin slice of tissue cut from a sample of a normal tissue or of a tumor.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Variable regions" or "V region" as used herein means the segment of IgG chains which is variable in sequence between different antibodies. It extends to Kabat residue 109 in the light chain and 113 in the heavy chain.

"RECIST 1.1 Response Criteria" as used herein means the definitions set forth in Eisenhauer, E. A. et al., *Eur. J. Cancer* 45:228-247 (2009) for target lesions or non-target lesions, as appropriate based on the context in which response is being measured.

II. PD-1 Antibodies and Antigen Binding Fragments Useful in the Invention

Examples of mAbs that bind to human PD-1, useful in the treatment methods, compositions, and uses of the invention, are described in U.S. Pat. Nos. 7,521,051, 8,008,449, and 8,354,509. Specific anti-human PD-1 mAbs useful as the PD-1 antagonist in the treatment methods, compositions, and uses of the present invention include: pembrolizumab (formerly known as MK-3475, SCH 900475 and lambrolizumab), a humanized IgG4 mAb with the structure described in *WHO Drug Information*, Vol. 27, No. 2, pages 161-162 (2013) and which comprises the heavy and light chain amino acid sequences shown in FIG. 1, and the humanized antibodies h409A11, h409A16 and h409A17, which are described in WO 2008/156712 and in Table 3.

In some embodiments of the treatment methods, compositions, kits and uses of the present invention, the anti-PD-1 antibody, or antigen binding fragment thereof, comprises: (a) light chain CDRs comprising a sequence of amino acids as set forth in SEQ ID NOs: 1, 2 and 3 and heavy chain CDRs comprising a sequence of amino acids as set forth in SEQ ID NOs: 6, 7 and 8; or (b) light chain CDRs comprising a sequence of amino acids as set forth in SEQ ID NOs: 11, 12 and 13 and heavy chain CDRs comprising a sequence of amino acids as set forth in SEQ ID NOs: 14, 15 and 16. In some embodiments of the invention, the anti-PD-1 antibody or antigen binding fragment thereof is a human antibody. In other embodiments, the anti-PD-1 antibody or antigen binding fragment thereof is a humanized antibody. In other embodiments, the anti-PD-1 antibody or antigen binding fragment thereof is a chimeric antibody. In specific embodiments, the anti-PD-1 antibody or antigen binding fragment thereof is a monoclonal antibody.

In other embodiments of the treatment methods, compositions, kits and uses of the present invention, the PD-1 antibody, or antigen binding fragment thereof, specifically binds to human PD-1 and comprises (a) a heavy chain variable region comprising an amino acid sequence as set forth in SEQ ID NO:9, or a variant thereof, and (b) a light chain variable region comprising an amino acid sequence selected from the group consisting of SEQ ID NO:4 or a variant thereof, SEQ ID NO:22 or a variant thereof, and SEQ ID NO:23 or a variant thereof.

A variant of a heavy chain variable region sequence or full-length heavy chain sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence or full-length light chain sequence is identical to the reference sequence except having up to five conservative amino acid substitutions in the framework region (i.e., outside of the CDRs), and preferably has less than four, three or two conservative amino acid substitution in the framework region.

In another embodiment of the treatment methods, compositions, kits and uses of the present invention, the PD-1 antibody or antigen-binding fragment thereof is a monoclonal antibody which specifically binds to human PD-1 and comprises (a) a heavy chain comprising or consisting of a sequence of amino acids as set forth in SEQ ID NO: 10, or a variant thereof; and (b) a light chain comprising or consisting of a sequence of amino acids as set forth in SEQ ID NO:5, or a variant thereof, SEQ ID NO:24, or a variant thereof, or SEQ ID NO:25, or a variant thereof.

In yet another embodiment of the treatment methods, compositions and uses of the invention, the PD-1 antibody or antigen-binding fragment thereof is a monoclonal antibody which specifically binds to human PD-1 and comprises (a) a heavy chain comprising or consisting of a sequence of amino acids as set forth in SEQ ID NO: 10 and (b) a light chain comprising or consisting of a sequence of amino acids as set forth in SEQ ID NO:5.

Table 3 below provides a list of the amino acid sequences of exemplary anti-PD-1 mAbs for use in the treatment methods, compositions, kits and uses of the present invention.

TABLE 3

Exemplary anti-human PD-1 antibodies

A. Comprises light and heavy chain CDRs of hPD-1.09A in WO2008/156712 (light and heavy chain CDRs of pembrolizumab)

| | |
|---|---|
| CDRL1 | SEQ ID NO: 1 |
| CDRL2 | SEQ ID NO: 2 |
| CDRL3 | SEQ ID NO: 3 |
| CDRH1 | SEQ ID NO: 6 |
| CDRH2 | SEQ ID NO: 7 |
| CDRH3 | SEQ ID NO: 8 |

B. Comprises light and heavy chain CDRs of hPD-1.08A in WO2008/156712

| | |
|---|---|
| CDRL1 | SEQ ID NO: 11 |
| CDRL2 | SEQ ID NO: 12 |
| CDRL3 | SEQ ID NO: 13 |
| CDRH1 | SEQ ID NO: 14 |
| CDRH2 | SEQ ID NO: 15 |
| CDRH3 | SEQ ID NO: 16 |

C. Comprises the mature h109A heavy chain variable region ($V_H$) and one of the mature K09A light chain variable ($V_L$) regions in WO 2008/156712

| | |
|---|---|
| Heavy chain $V_H$ | SEQ ID NO: 9 ($V_H$ of pembrolizumab) |
| Light chain $V_L$ | SEQ ID NO: 4 ($V_L$ of pembrolizumab) or SEQ ID NO: 22 or SEQ ID NO: 23 |

TABLE 3-continued

Exemplary anti-human PD-1 antibodies

D. Comprises the mature 409 heavy chain and one of the mature K09A light chains in WO 2008/156712

| | |
|---|---|
| Heavy chain | SEQ ID NO: 10 (heavy chain of pembrolizumab) |
| Light chain | SEQ ID NO: 5 (light chain of pembrolizumab) or SEQ ID NO: 24 or SEQ ID NO: 25 |

III. Methods and Uses of the Invention

The invention provides a method of treating cancer in a human patient comprising administering about 400 mg of an anti-PD-1 antibody, or antigen-binding fragment thereof, to the patient once every about six weeks, wherein the anti-PD-1 antibody or antigen binding fragment thereof comprises: (a) light chain complementarity determining regions (CDRs) comprising a sequence of amino acids as set forth in SEQ ID NOs: 1, 2 and 3 and heavy chain CDRs comprising a sequence of amino acids as set forth in SEQ ID NOs: 6, 7 and 8; or (b) light chain CDRs comprising a sequence of amino acids as set forth in SEQ ID NOs:11, 12 and 13 and heavy chain CDRs comprising a sequence of amino acids as set forth in SEQ ID NOs: 14, 15 and 16. In particular embodiments of the invention, the anti-PD-1 antibody, or antigen-binding fragment thereof, is pembrolizumab.

In some embodiments of the invention, the anti-PD-1 antibody, or antigen binding fragment thereof, is administered to the patient about once every six weeks for 12 weeks or more. In other embodiments, the anti-PD-1 antibody, or antigen binding fragment thereof is administered to the patient once every six weeks for 18 weeks or more, 24 weeks or more, 30 weeks or more, 36 weeks or more, 42 weeks or more, 48 weeks or more, 54 weeks or more, 60 weeks or more, 66 weeks or more, 72 weeks or more, 78 weeks or more, 84 weeks or more, or 90 weeks or more.

In a first embodiment (Embodiment E1), the invention comprises a method of treating cancer in a human patient comprising administering 400 mg of an anti-PD-1 antibody (e.g., pembrolizumab), or antigen binding fragment thereof, to the patient once every approximately six weeks.

In a second embodiment (Embodiment E2), the invention comprises a method of treating unresectable or metastatic melanoma in a human patient comprising administering 400 mg of an anti-PD-1 antibody (e.g., pembrolizumab), or antigen binding fragment thereof, to the patient once every approximately six weeks.

In a third embodiment (Embodiment E3), the invention comprises a method of treating metastatic non-small cell lung cancer (NSCLC) in a human patient comprising administering 400 mg of an anti-PD-1 antibody (e.g., pembrolizumab), or antigen binding fragment thereof, to the patient once every approximately six weeks.

In a sub-embodiment of Embodiment E3 (Embodiment E3-A), the patient has a tumor with high PD-L1 expression [(Tumor Proportion Score (TPS)≥50%)] and was not previously treated with platinum-containing chemotherapy.

In a further sub-embodiment of Embodiment E3 (Embodiment E3-B), the patient has a tumor with PD-L1 expression (TPS≥1%) and was previously treated with platinum-containing chemotherapy. In specific embodiments of Embodiment E3-B, the patient had disease progression on or after receiving platinum-containing chemotherapy.

In another sub-embodiment of Embodiment E3 (Embodiment E3-C), the patient has a tumor with PD-L1 expression (TPS≥1%) and was not previously treated with platinum-containing chemotherapy.

In yet another sub-embodiment of Embodiment E3 (Embodiment E3-D), the patient's tumor is not tested for PD-L1 expression. In this embodiment, the patient is treated with the anti-PD-1 antibody, or antigen binding fragment thereof, regardless of PD-L1 expression. In specific embodiments, the patient was not previously treated with platinum-containing chemotherapy.

In certain embodiments of Embodiment E3 (including Embodiment E3-A, E3-B, and E3-C), the PD-L1 TPS is determined by an FDA-approved test.

In certain embodiments of Embodiment E3 (including Embodiment E3-A, E3-B, E3-C and E3-D), the patient's tumor has no EGFR or ALK genomic aberrations.

In certain embodiments of Embodiment E3 (including Embodiment E3-A, E3-B, E3-C and E3-D), the patient's tumor has an EGFR or ALK genomic aberration and had disease progression on or after receiving treatment for the EGFR or ALK aberration(s) prior to receiving the anti-PD-1 antibody, or antigen binding fragment thereof.

In a fourth embodiment (Embodiment E4), the invention comprises a method of treating metastatic non-small cell lung cancer (NSCLC) in a human patient comprising: (1) administering 400 mg of an anti-PD-1 antibody (e.g., pembrolizumab), or antigen binding fragment thereof, to the patient once every approximately six weeks, and (2) administering pemetrexed and carboplatin to the patient. In sub-embodiments of Embodiment E4, the patient was not previously treated with an anti-cancer therapeutic prior to starting the combination treatment regimen with the anti-PD-1 antibody, or antigen binding fragment thereof, pemetrexed and carboplatin.

In certain embodiments of Embodiment E3 and E4 (including sub-embodiments thereof), the patient has nonsquamous non-small cell lung cancer.

In sub-embodiments of Embodiment E4, pemetrexed is administered to the patient in an amount of 500 mg/M2

In sub-embodiments of Embodiment E4, pemetrexed is administered to the patient via intravenous infusion every 21 days. In specific embodiments, the infusion time is about 10 minutes.

In sub-embodiments of Embodiment E4 (Embodiment E4-A), the invention further comprises administering about 400 μg to about 1000 μg of folic acid to the patient once per day, beginning about 7 days prior to administering pemetrexed to the patient and continuing until about 21 days after the patient is administered the last dose of pemetrexed. In certain embodiments the folic acid is administered orally.

In sub-embodiments of Embodiments E4 and E4-A (Embodiment E4-B), the invention further comprises administering about 1 mg of vitamin $B_{12}$ to the patient about 1 week prior to the first administration of pemetrexed and about every three cycles of pemetrexed administration (i.e., approximately every 9 weeks). In certain embodiments the vitamin $B_{12}$ is administered intramuscularly.

In sub-embodiments of Embodiments E4, E4-A and E4-B (Embodiment E4-C), the invention further comprises administering about 4 mg of dexamethasone to the patient twice a day on the day before, the day of, and the day after pemetrexed administration. In certain embodiments the dexamethasone is administered orally.

In a fifth embodiment (Embodiment E5), the invention comprises a method of treating recurrent or metastatic head and neck squamous cell cancer (HNSCC) in a human patient comprising administering 400 mg of an anti-PD-1 antibody (e.g., pembrolizumab), or antigen binding fragment thereof, to the patient once every approximately six weeks.

In sub-embodiments of Embodiment E5, the patient was previously treated with platinum-containing chemotherapy. In certain embodiments, the patient had disease progression on or after platinum-containing chemotherapy.

In a sixth embodiment (Embodiment E6), the invention comprises a method of treating refractory classical Hodgkin lymphoma (cHL) in a human patient comprising administering 400 mg of an anti-PD-1 antibody (e.g., pembrolizumab), or antigen binding fragment thereof, to the patient once every approximately six weeks.

In a seventh embodiment (Embodiment E7), the invention comprises a method of treating classical Hodgkin lymphoma (cHL) in a human patient comprising administering 400 mg of an anti-PD-1 antibody (e.g., pembrolizumab), or antigen binding fragment thereof, to the patient once every approximately six weeks, wherein the patient has relapsed after (a) one or more lines of therapy for cHL, (b) 2 or more lines of therapy for cHL, or (c) 3 or more lines of therapy for cHL.

In sub-embodiments of Embodiments E6 and E7, the patient is an adult patient.

In alternative sub-embodiments of Embodiments E6 and E7, the patient is a pediatric patient.

In an eighth embodiment (Embodiment E8), the invention comprises a method of treating locally advanced or metastatic urothelial carcinoma in a human patient comprising administering 400 mg of an anti-PD-1 antibody (e.g., pembrolizumab), or antigen binding fragment thereof, to the patient once every approximately six weeks.

In sub-embodiments of Embodiment E8, the patient is not eligible for cisplatin-containing chemotherapy.

In sub-embodiments of Embodiment E8, the patient had disease progression during or following platinum-containing chemotherapy or within 12 months of neoadjuvant or adjuvant treatment with platinum-containing chemotherapy.

In sub-embodiments of Embodiment E8, the patient's tumor expresses PD-L1 (CPS≥10).

In a ninth embodiment (Embodiment E9), the invention comprises a method of treating unresectable or metastatic, microsatellite instability-high (MSI-H) or mismatch repair (MMR) deficient solid tumors in a human patient comprising administering 400 mg of an anti-PD-1 antibody (e.g., pembrolizumab), or antigen binding fragment thereof, to the patient once every approximately six weeks.

In a sub-embodiment of Embodiment E9, the patient had disease progression following prior anti-cancer treatment.

In a tenth embodiment (Embodiment E10), the invention comprises a method of treating unresectable or metastatic, MSI-H or MMR deficient colorectal cancer in a human patient comprising administering 400 mg of an anti-PD-1 antibody (e.g., pembrolizumab), or antigen binding fragment thereof, to the patient once every approximately six weeks.

In a sub-embodiment of Embodiment E10, the patient had disease progression following prior treatment with a fluoropyrimidine, oxaliplatin, and irinotecan.

In an eleventh embodiment (Embodiment E11), the invention comprises a method of treating recurrent locally advanced or metastatic gastric cancer in a human patient comprising administering 400 mg of an anti-PD-1 antibody (e.g., pembrolizumab), or antigen binding fragment thereof, to the patient once every approximately six weeks.

In a twelfth embodiment (Embodiment E12), the invention comprises a method of treating recurrent locally advanced or metastatic gastroesophageal junction adenocarcinoma in a human patient comprising administering 400 mg of an anti-PD-1 antibody (e.g., pembrolizumab), or antigen binding fragment thereof, to the patient once every approximately six weeks.

In sub-embodiments of Embodiments E11 and E12, the patient's tumor expresses PD-L1 [Combined Positive Score (CPS)≥1].

In sub-embodiments of Embodiments E11 and E12, the patient had disease progression on or after one or more prior lines of therapy. In specific embodiments, the prior lines of therapy include fluoropyrimidine and platinum-containing chemotherapy.

In sub-embodiments of Embodiments E11 and E12, the patient had disease progression on or after two or more prior lines of therapy including fluoropyrimidine- and platinum-containing chemotherapy.

In sub-embodiments of Embodiments E11 and E12, the patient had disease progression on or after one or more prior lines of therapy including HER2/neu-targeted therapy.

In sub-embodiments of Embodiments E11 and E12, the patient had disease progression on or after two or more prior lines of therapy including HER2/neu-targeted therapy.

In a thirteenth embodiment (Embodiment E13), the invention comprises a method of treating cancer in a human patient comprising administering 400 mg of an anti-PD-1 antibody (e.g. pembrolizumab), or antigen binding fragment thereof, to the patient once every approximately six weeks, wherein the patient has a cancer selected from the group consisting of: melanoma, lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer.

In a fourteenth embodiment (Embodiment E14), the invention comprises a method of treating cancer in a human patient comprising administering 400 mg of an anti-PD-1 antibody (e.g. pembrolizumab), or antigen binding fragment thereof, to the patient once every approximately six weeks, wherein the patient has small-cell lung cancer.

In a fifteenth embodiment (Embodiment E15), the invention comprises a method of treating non-Hodgkin lymphoma in a human patient comprising administering 400 mg of an anti-PD-1 antibody (e.g. pembrolizumab), or antigen binding fragment thereof, to the patient once every approximately six weeks.

In a sub-embodiment of Embodiment E15, the non-Hodgkin lymphoma is primary mediastinal large B-cell lymphoma (PMBCL). In some embodiments where the patient has PMBCL, the patient has refractory PMBCL. In some embodiments, the patient has relapsed after one or more prior lines of therapy. In some embodiments, the patient has relapsed after two or more prior lines of therapy. In some embodiments, the patient was not previously treated with another line of therapy.

In a sixteenth embodiment (Embodiment E16), the invention comprises a method of treating metastatic squamous NSCLC in a human patient comprising: (1) administering 400 mg of an anti-PD-1 antibody (e.g., pembrolizumab), or antigen binding fragment thereof, to the patient once every approximately six weeks, and (2) administering (i) carboplatin and paclitaxel, or (ii) carboplatin and nab-paclitaxel to the patient.

In a seventeenth embodiment (Embodiment E17), the invention comprises a method of treating Merkel cell carcinoma (MCC) in a human patient comprising administering 400 mg of an anti-PD-1 antibody (e.g., pembrolizumab), or antigen binding fragment thereof, to the patient once every approximately six weeks. In particular sub-embodiments of Embodiment E17, the cancer is recurrent, locally advanced MCC. In particular sub-embodiments of Embodiment E17, the cancer is metastatic MCC.

In sub-embodiments of Embodiment E17, the patient is an adult patient. In alternative sub-embodiments of Embodiment E17, the patient is a pediatric patient.

In a eighteenth embodiment (Embodiment E18), the invention comprises a method for adjuvant therapy of melanoma in a human patient comprising administering 400 mg of an anti-PD-1 antibody (e.g., pembrolizumab), or antigen binding fragment thereof, to a patient once every approximately six weeks, wherein the patient has previously had one or more melanoma lesions resected. In sub-embodiments of Embodiment E18, the method comprises treating resected high-risk stage III melanoma.

In a nineteenth embodiment (Embodiment E19), the invention comprises a method of treating hepatocellular carcinoma (HCC) in a human patient comprising administering 400 mg of an anti-PD-1 antibody (e.g., pembrolizumab), or antigen binding fragment thereof, to the patient once every approximately six weeks. In some embodiments of Embodiment E19, the patient was previously treated with sorafenib.

In a twentieth embodiment (Embodiment E20), the invention comprises a method of treating renal cell carcinoma (RCC) in a human patient comprising administering 400 mg of an anti-PD-1 antibody (e.g., pembrolizumab), or antigen binding fragment thereof, to the patient once every approximately six weeks.

In sub-embodiments, of Embodiment E20, the cancer is advanced clear cell RCC.

In sub-embodiments of Embodiment E20, the patient has advanced or metastatic renal cell carcinoma (RCC).

In sub-embodiments, of Embodiment E20 (Embodiment E20A), the patient is further treated with axitinib. In sub-embodiments of the invention, axitinib is taken orally.

In particular embodiments of Embodiment E20A, 5 mg axitinib is taken by the patient approximately every 12 hours or twice a day.

In alternative embodiments of Embodiment E20A, the axitinib dosage is 2.5 mg, 3 mg, 7 mg, or 10 mg twice daily.

In a twenty-first embodiment (Embodiment E21), the invention comprises a method of treating breast cancer in a human patient comprising administering 400 mg of an anti-PD-1 antibody (e.g., pembrolizumab), or antigen binding fragment thereof, to the patient once every approximately six weeks.

In a sub-embodiment of Embodiment E21, the breast cancer is triple negative breast cancer.

In a sub-embodiment of Embodiment E21, the breast cancer is ER+/HER2− breast cancer.

In a twenty-second embodiment (Embodiment E22), the invention comprises a method of treating nasopharyngeal cancer in a human patient comprising administering 400 mg of an anti-PD-1 antibody (e.g., pembrolizumab), or antigen binding fragment thereof, to the patient once every approximately six weeks.

In a twenty-third embodiment (Embodiment E23), the invention comprises a method of treating thyroid cancer in a human patient comprising administering 400 mg of an anti-PD-1 antibody (e.g., pembrolizumab), or antigen binding fragment thereof, to the patient once every approximately six weeks.

In a twenty-fourth embodiment (Embodiment E24), the invention comprises a method of treating salivary cancer in a human patient comprising administering 400 mg of an anti-PD-1 antibody (e.g., pembrolizumab), or antigen binding fragment thereof, to the patient once every approximately six weeks.

In a twenty-fifth embodiment (Embodiment E25), the invention comprises a method of treating cancer in a human patient comprising administering 400 mg of an anti-PD-1 antibody (e.g., pembrolizumab), or antigen binding fragment thereof, to the patient once every approximately six weeks, wherein the cancer is selected from the group consisting of: melanoma, non-small cell lung cancer, relapsed or refractory classical Hodgkin lymphoma, primary mediastinal large B-cell lymphoma, head and neck squamous cell cancer, urothelial carcinoma, esophageal cancer, gastric cancer, cervical cancer, PMBCL, MSI-H cancer, hepatocellular carcinoma, and Merkel cell carcinoma.

In a twenty-sixth embodiment (Embodiment E26), the invention comprises a method of treating cancer in a human patient comprising administering 400 mg of an anti-PD-1 antibody (e.g., pembrolizumab), or antigen binding fragment thereof, to the patient once every approximately six weeks, wherein the cancer is a Heme malignancy.

In a sub-embodiment of Embodiment E26, the heme malignancy is selected from the group consisting of: acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (MCL-1), myelodysplastic syndrome (MDS), non-Hodgkin lymphoma (NHL), and small lymphocytic lymphoma (SLL).

In a twenty-seventh embodiment (Embodiment E27), the invention comprises a method of treating cancer in a human patient comprising administering 400 mg of an anti-PD-1 antibody (e.g., pembrolizumab), or antigen binding fragment thereof, to the patient once every approximately six weeks, wherein the patient has a tumor with a high mutational burden.

In specific embodiments, a high mutational burden is at least about 10 mutations per megabase of genome examined, at least about 11 mutations per megabase of genome examined, at least about 12 mutations per megabase of genome examined, or at least about 13 mutations per megabase of genome examined.

In a twenty-eighth embodiment (Embodiment E28), the invention comprises a method of treating esophageal cancer in a human patient comprising administering 400 mg of an anti-PD-1 antibody (e.g., pembrolizumab), or antigen binding fragment thereof, to the patient once every approximately six weeks.

In sub-embodiments of Embodiment E28, the patient progressed with one previous line of standard therapy prior to receiving the anti-PD-1 antibody, or antigen binding fragment thereof. In a further embodiment, the patient progressed with one or more lines of standard therapy prior to receiving the anti-PD-1 antibody, or antigen binding fragment thereof. In another embodiment, the patient progressed with two or more lines of standard therapy prior to receiving the anti-PD-1 antibody, or antigen binding fragment thereof. In particular embodiments, the standard therapy includes one or more of: paclitaxel, docetaxel, or irinotecan.

In sub-embodiments of Embodiment E28, the patient has advanced or metastatic adenocarcinoma or squamous cell carcinoma of the esophagus.

In sub-embodiments of Embodiment E28, the patient has advanced or metastatic Siewert type I adenocarcinoma of the esophagogastric junction.

In sub-embodiments of Embodiment E28, the patient's tumor expresses PD-L1 (Combined Positive Score [CPS] ≥10).

In a twenty-ninth embodiment (Embodiment E29), the invention comprises a method of treating high-risk non-muscle invasive bladder cancer (NMIBC) in a human patient comprising administering 400 mg of an anti-PD-1 antibody (e.g., pembrolizumab), or antigen binding fragment thereof, to the patient once every approximately six weeks. In some embodiments, the patient has NMIBC with carcinoma insitu (CIS) or CIS plus papillary disease.

In a sub-embodiment of Embodiment E29, the patient was previously treated with standard therapy prior to being treated with the anti-PD-1 antibody, or antigen binding fragment thereof. In some embodiments, the prior therapy is *Bacillus* Calmette-Guerin (BCG) therapy. In particular embodiments, the patient did not respond to BCG therapy. In some embodiments, the patient was ineligible for radical cystectomy or chose not to undergo radical cystectomy.

In any of the methods of the invention described above (including Embodiments E1-E29), the PD-1 antibody or antigen binding fragment is any of the antibodies or antigen-binding fragments described in Section II of the Detailed Description of the Invention "PD-1 Antibodies and Antigen Binding Fragments Useful in the Invention" herein. In some embodiments, the anti-PD-1 antibody is pembrolizumab or an antigen-binding fragment thereof, or an antibody which cross competes with pembrolizumab for binding to human PD-1. In some embodiments, the anti-PD-1 antibody is a variant of pembrolizumab; i.e. an antibody or antigen-binding fragment having light chain CDRs comprising a sequence of amino acids as set forth in SEQ ID NOs: 1, 2 and 3 and heavy chain CDRs comprising a sequence of amino acids as set forth in SEQ ID NOs: 6, 7 and 8.

In any of the methods of the invention described above (including Embodiments E1-E29), the PD-1 antibody or antigen binding fragment is administered to the patient once every approximately six weeks. In particular embodiments, the PD-1 antibody or antigen binding fragment is administered to the patient every six weeks, every six weeks 5 days, 4 days, 3 days, 2 days or 1 day.

In embodiments of any of the methods of treatment herein, a patient is administered an intravenous (IV) infusion of a medicament comprising any of the anti-PD-1 antibodies or antigen-binding fragments described herein.

In alternative embodiments of any of the methods of treatment herein, the patient is administered (e.g., by a clinician) or administers any of the anti-PD-1 antibodies or antigen-binding fragments subcutaneously.

In any of the methods described herein, including Embodiment E1-E29, and sub-embodiments thereof, the method may further comprise one or more "additional therapeutic agents" (as used herein, "additional therapeutic agent" refers to an additional agent relative to the anti-PD-1 antibody or antigen-binding fragment thereof). The additional therapeutic agent may be, e.g., a chemotherapeutic other than an anti-PD-1 antibody, a biotherapeutic agent (including but not limited to antibodies to CTLA4, VEGF, EGFR, Her2/neu, VEGF receptors, other growth factor receptors, CD20, CD40, CD-40L, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

As noted above, in some embodiments of the methods of the invention, the method further comprises administering an additional therapeutic agent. In particular embodiments, the additional therapeutic agent is an anti-CTLA4 antibody or antigen binding fragment thereof, an anti-LAG3 antibody or antigen binding fragment thereof, an anti-GITR antibody, or antigen binding fragment thereof, an anti-TIGIT antibody, or antigen binding fragment thereof, an anti-CD27 antibody or antigen binding fragment thereof, an anti-ILT3 antibody, or antigen binding fragment thereof, or an anti-ILT4 antibody, or antigen binding fragment thereof. In one embodiment, the additional therapeutic agent is a Newcastle disease viral vector expressing IL-12. In a further embodiment, the additional therapeutic agent is dinaciclib. In another embodiment, the additional therapeutic agent is navarixin. In a further embodiment, the additional therapeutic agent is vicriviroc.

In a further embodiment, the additional therapeutic agent is an oncolytic virus. In one embodiment, the additional therapeutic agent is Coxsackievirus or CVA21. In one embodiment, the additional therapeutic agent is CAV-ATAK™ In yet another embodiment, the additional therapeutic agent is a STING agonist.

In a further embodiment, the additional therapeutic agent is an IL-27 antagonist. In one embodiment, the additional therapeutic agent is a PARP inhibitor. In one embodiment, the additional therapeutic agent is a multi-kinase inhibitor. In one embodiment, the additional therapeutic agent is a MEK inhibitor. In one embodiment, the additional therapeutic agent is a 4-1BB agonist.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

In some embodiments which comprise a step of administering an additional therapeutic agent (i.e., in addition to the PD-1 antibody (e.g., pembrolizumab) or antigen-binding fragment thereof), the additional therapeutic agent in the combination therapy may be administered using the same dosage regimen (dose, frequency and duration of treatment) that is typically employed when the agent is used as monotherapy for treating the same cancer. In other embodiments, the patient receives a lower total amount of the additional therapeutic agent in the combination therapy than when that agent is used as monotherapy, e.g., smaller doses, less frequent doses, and/or shorter treatment duration.

The additional therapeutic agent in a combination therapy can be administered orally, intratumorally, or parenterally, including the intravenous, intramuscular, intraperitoneal, subcutaneous, rectal, topical, and transdermal routes of administration. For example, the combination treatment may comprise an anti-PD-1 antibody or antigen binding fragment thereof, and an anti-CTLA antibody or antigen binding fragment thereof, both of which may be administered intravenously or subcutaneously, as well as a chemotherapeutic agent, which may be administered orally.

A combination therapy of the invention may be used prior to or following surgery to remove a tumor and may be used prior to, during or after radiation therapy. A combination therapy of the invention may also be used when a patient's tumor is non-resectable.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced.

A combination therapy of the invention may be used to treat a tumor that is large enough to be found by palpation or by imaging techniques well known in the art, such as MRI, ultrasound, or CAT scan. In some embodiments, a combination therapy of the invention is used to treat an advanced stage tumor having dimensions of at least about 200 mm$^3$, 300 mm$^3$, 400 mm$^3$, 500 mm$^3$, 750 mm$^3$, or up to 1000 mm$^3$.

In some embodiments, a combination therapy of the invention is administered to a human patient who has a cancer that expresses PD-L1. In some embodiments, PD-L1 expression is detected using a diagnostic anti-human PD-L1 antibody, or antigen binding fragment thereof, in an IHC assay on an FFPE or frozen tissue section of a tumor sample removed from the patient. A patient's physician may order a diagnostic test to determine PD-L1 expression in a tumor tissue sample removed from the patient prior to initiation of treatment with the anti-PD-1 antibody, or antigen-binding fragment thereof, but it is envisioned that the physician could order the first or subsequent diagnostic tests at any time after initiation of treatment, such as for example after completion of a treatment cycle.

Selecting a dosage of the additional therapeutic agent depends on several factors, including the serum or tissue turnover rate of the entity, the level of symptoms, the immunogenicity of the entity, and the accessibility of the target cells, tissue or organ in the individual being treated. The dosage of the additional therapeutic agent should be an amount that provides an acceptable level of side effects. Accordingly, the dose amount and dosing frequency of each additional therapeutic agent (e.g. biotherapeutic or chemotherapeutic agent) will depend in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies andPeptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000)*New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

IV. Compositions and Kits

The invention also relates to compositions comprising a dosage of an anti-PD-1 antibody (e.g., pembrolizumab) or antigen binding fragment thereof and a pharmaceutically acceptable carrier or excipient, wherein the dosage is about 400 mg. The anti-PD-1 antibody may be produced, for example, in CHO cells using conventional cell culture and recovery/purification technologies.

In embodiments of the invention, the composition further comprises histidine buffer at about pH 5.0 to pH 6.0. In particular embodiments, the histidine is present in a concentration of about 10 mM.

In embodiments of the invention, the composition further comprises sucrose. In particular embodiments, the sucrose is present in a concentration of about 70 mg/mL.

In embodiments of the invention, the composition further comprises polysorbate 80. In particular embodiments, the polysorbate 80 is present in a concentration of about 0.2 mg/mL.

In some embodiments, the composition comprises 10 mM histidine, pH 5.5, 7% sucrose, 0.02% polysorbate 80, and 400 mg of the anti-PD-1 antibody or antigen-binding fragment thereof.

In embodiments of the invention, the composition is liquid.

In alternative embodiments, the composition is lyophilized.

In the compositions of the invention, the anti-PD-1 antibody or antigen binding fragment thereof can be any of the antibodies and antigen binding fragments described herein, i.e. described in Section II of the Detailed Description of the Invention "PD-1 Antibodies and Antigen Binding Fragments Useful in the Invention" (e.g. pembrolizumab).

In some embodiments, a composition comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising pembrolizumab that are suitable for use in the present invention.

The invention also relates to a kit for treating a patient with cancer, the kit comprising: (a) 400 mg of an anti-PD-1 antibody or antigen binding fragment thereof, and (b) instructions for using the anti-PD-1 antibody or antigen binding fragment thereof in any of the methods for treating cancer described herein.

In any of the kits of the invention, the PD-1 antibody or antigen binding fragment can be any of the antibodies or antigen-binding fragments described in Section II of the Detailed Description of the Invention "PD-1 Antibodies and Antigen Binding Fragments Useful in the Invention".

The kits of the invention may provide the anti-PD-1 or antigen-binding fragments thereof in a container and a package insert. The container contains at least one dose (i.e. about 400 mg) of a medicament comprising an anti-PD-1 antibody, or antigen binding fragment thereof, and the package insert, or label, which comprises instructions for treating a patient with cancer using the medicament. The container may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some preferred embodiments of the kit, the instructions state that the medicament is intended for use in treating a patient having a tumor, wherein the tumor expresses PD-L1 by, e.g., an IHC assay. In some embodiments, the tumor has a tumor proportion score (TPS) of ≥1% PD-L1. In another embodiment, the tumor has a TPS of ≥50% PD-L1. A PD-L1 TPS is the number of tumor cells in a sample expressing PD-L1. In further embodiments, the tumor has a TPS of ≥5% PD-L1, ≥10 PD-L1, ≥15% PD-L1, ≥20% PD-L1, ≥25% PD-L1, ≥30% PD-L1, ≥35% PD-L1, ≥40% PD-L1, or ≥45% PD-L1. In another embodiment, the patient's tumor expresses PD-L1 with a CPS of ≥10%. In another embodiment, the patient's tumor expresses PD-L1 with a CPS of ≥5%. In another embodiment, the patient's tumor expresses PD-L1 with a CPS of ≥1%.

These and other aspects of the invention, including the exemplary specific embodiments listed below, will be apparent from the teachings contained herein.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol. 1*, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) Nature Biotechnol. 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Mull er-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.). Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

A Six-Weekly (Q6W) Dosing Schedule for Pembrolizumab Across Multiple Tumor Types Based on an Evaluation Using Modeling and Simulation Pembrolizumab, an anti-PD-1 checkpoint inhibitor currently approved for use in multiple cancer indications, has demonstrated safety and efficacy when administered at a dose of either 200 mg or 2 mg/kg Q3W. An alternative extended dosing regimen would provide the benefits of convenience and flexibility to both patients and prescribers. The robust characterization of pembrolizumab pharmacokinetics (PK) and exposure (concentration)-response (E-R) relationships for both efficacy and safety allow the use of model-based approaches to support alternative dosing regimens for pembrolizumab.

The dose for a Q6W schedule of pembrolizumab was selected by matching exposures with the approved Q3W (200 mg and 2 mg/kg) regimens after PK steady state is achieved; the efficacy and safety between regimens were bridged based on knowledge of E-R. PK exposures were simulated up to 24 weeks of dosing, to ensure steady state in all subjects, using the established population PK model (with time dependent elimination) of pembrolizumab that adequately described PK across multiple tumor types. Efficacy was bridged using exposure metrics at steady state, AUCss or time-averaged concentration (Cavg,ss) and trough concentrations (Cmin,ss), which were compared between regimens. The safety profile of pembrolizumab at the Q6W schedule was bridged by ensuring that the predicted peak concentrations at steady state (Cmax,ss) are below those of the maximum clinically administered and well-tolerated dose of 10 mg/kg Q2W.

Figure 3:
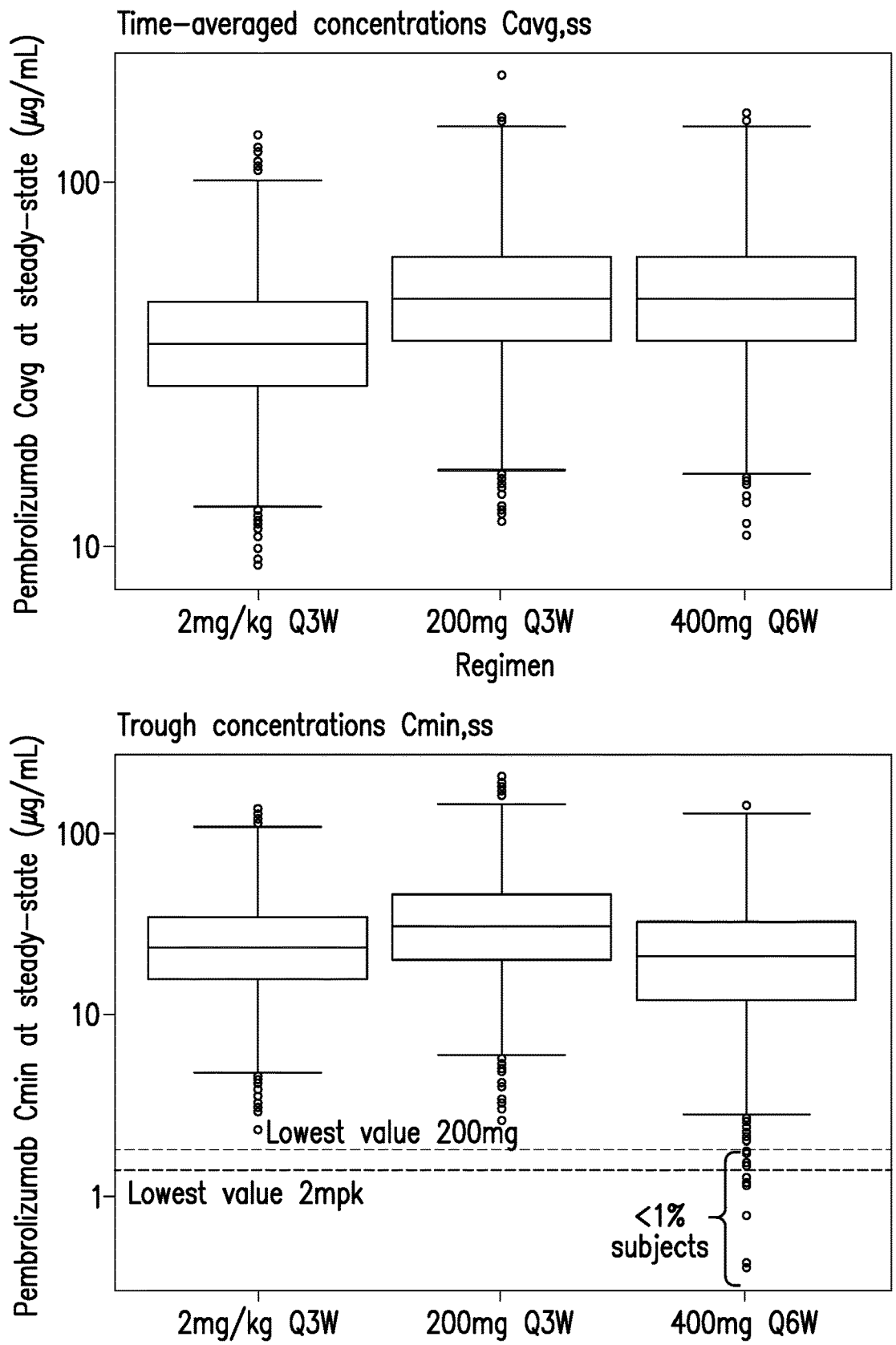
FIG. 3 shows that pembrolizumab exposures (Cavg and Cmin) at steady state are similar for 400 mg Q6W relative to 2 mg/kg Q3W and 200 mg Q3W.
Figure 4A:
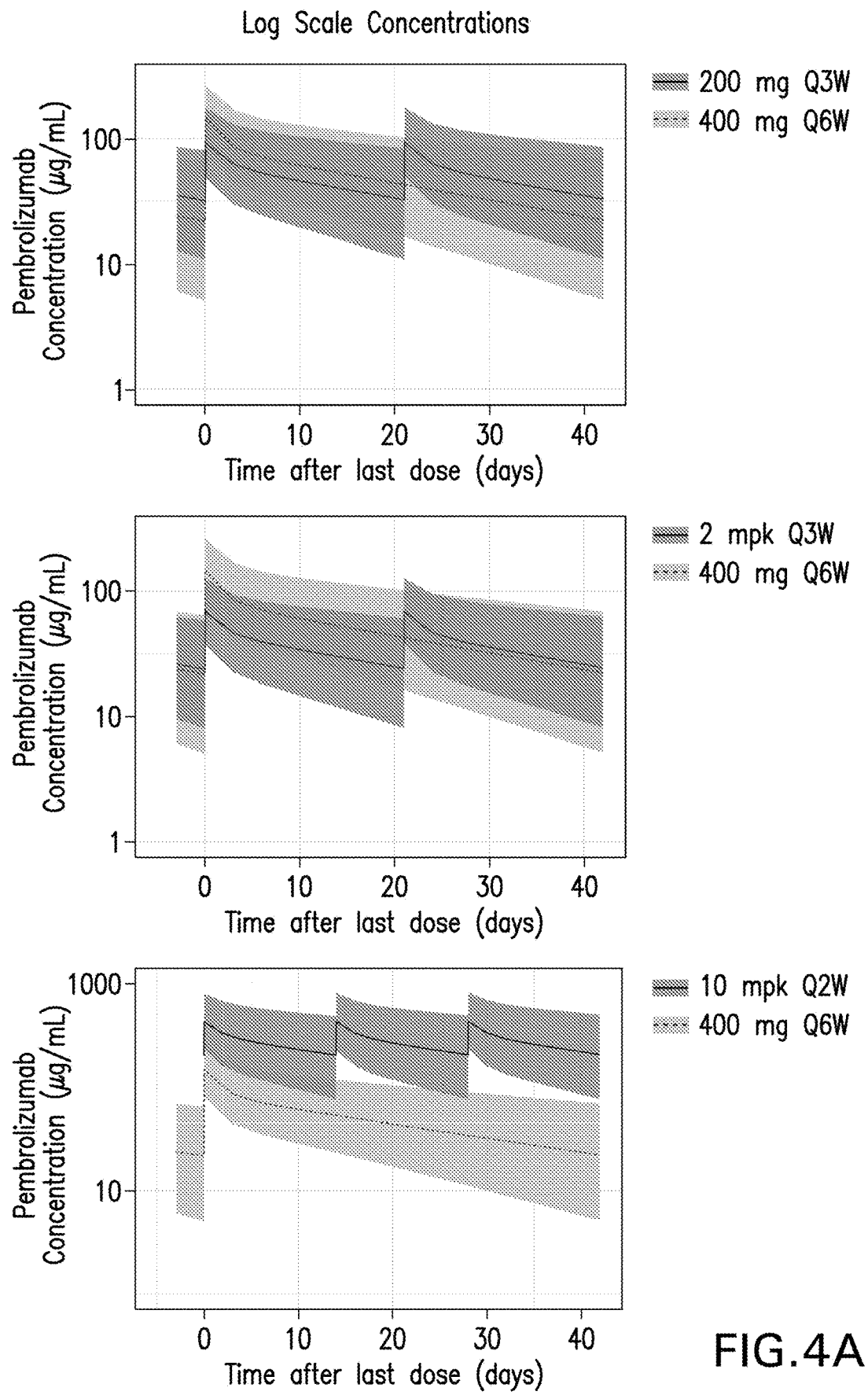
FIGS. 4A and 4B show the pembrolizumab pharmacokinetic profiles at steady state for the 400 mg Q6W dosing regimen compared to the 200 mg, Q3W, flat dosing regimen (top), the Q3W, 2 mg/kg weight-based dosing regimen (middle), and the Q2W, 10 mg/kg weight-based dosing regimen (bottom). Results are provided for log scale concentrations (FIG. 4A) and linear scale concentrations (FIG. 4B).
Figure 4B:
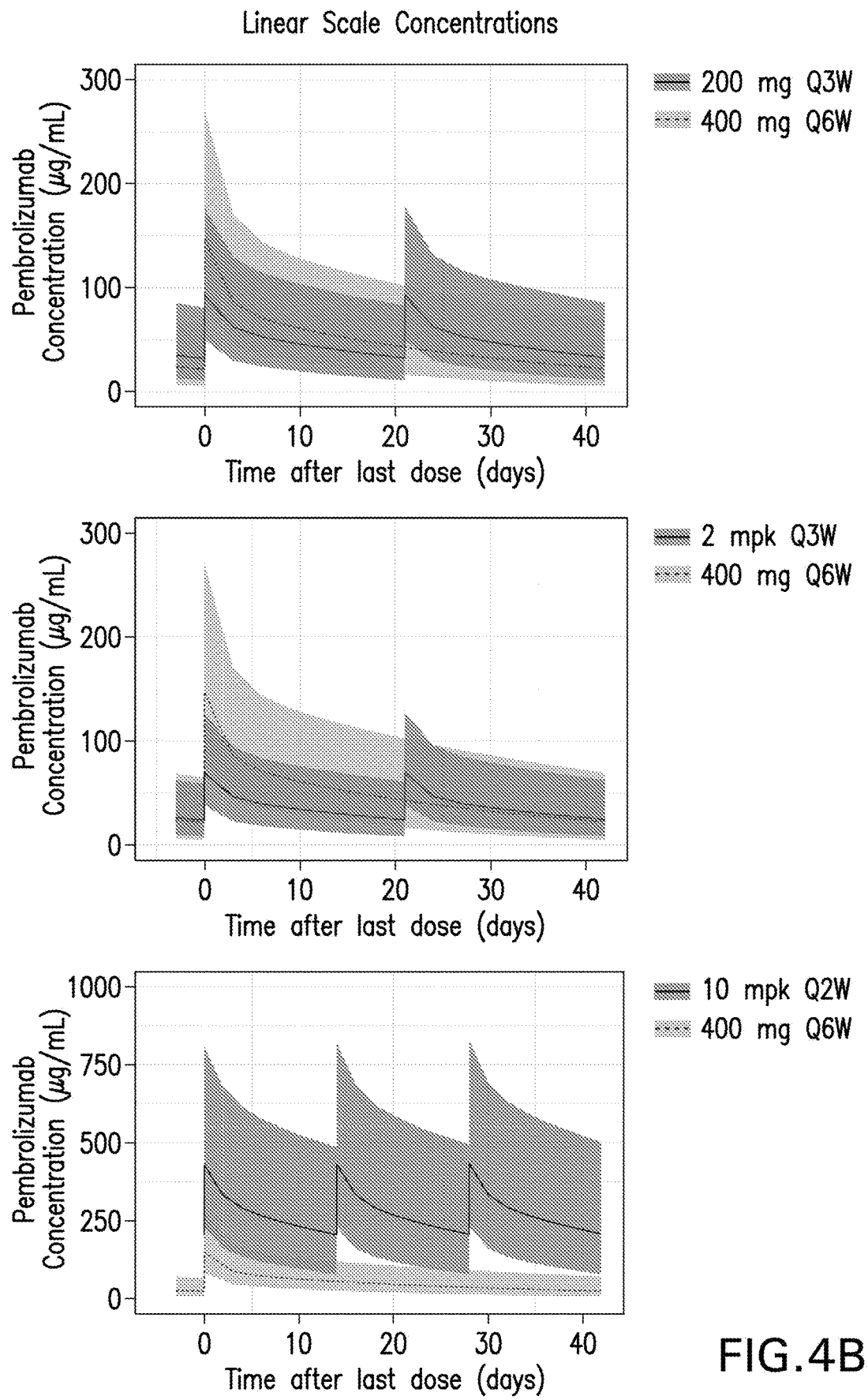

The PK of pembrolizumab after administration of 400 mg Q6W is predicted to follow a similar profile as the PK at the approved 200 mg Q3W and 2 mg/kg Q3W dosing regimens (see FIG. 4). The exposure metrics as compared between regimens are summarized in Table 4. The 400 mg Q6W dosing regimen of pembrolizumab was selected based on similar predicted exposures (Cavg,ss or AUCss, geometric mean (GM) ~1% higher) compared with those achieved at 200 mg Q3W (see FIG. 3). Less than 1% subjects were predicted to have Cmin,ss that are lower in comparison with those at 200 mg Q3W and 2 mg/kg Q3W (FIG. 3). The predicted Cmax,ss for 400 mg Q6W are well below (GM ~65% lower) that achieved with 10 mg/kg Q2W, which has been shown to have acceptable safety across multiple tumor types (see FIG. 2). Given the similar exposure profiles and the established, flat E-R relationships for pembrolizumab at clinically tested doses, the clinical outcomes achieved with 400 mg Q6W are expected to be similar to those with 200 mg Q3W across tumor types.

Based on the modeling and simulation approach used herein, it is expected that a 400 mg Q6W dosing regimen for pembrolizumab would lead to PK exposures that are similar to the approved 200 mg Q3W and 2 mg/kg dosing regimens. PK simulations demonstrate that in terms of pembrolizumab exposures—Average concentration over the dosing interval (Cavg) (or area under the curve [AUC]) at 400 mg Q6W was similar to that at the approved 200 mg Q3W dose, thus bridging efficacy between dosing regimens. Trough concentrations (Cmin) at 400 mg Q6W were generally within the range of those achieved with 2 mg/kg or 200 mg Q3W in the majority (>99%) of patients. Peak concentrations (Cmax) at 400 mg Q6W were well below the Cmax for the highest clinically tested dose of 10 mg/kg Q2W, supporting that the safety profile for 400 mg Q6W should be comparable to the established safety profile of pembrolizumab. Exposure-response (E-R) for pembrolizumab was demonstrated to be flat across indications, and OS predictions in melanoma and NSCLC demonstrate that efficacy at 400 mg Q6W is expected to be similar to that at 200 mg or 2 mg/kg Q3W, given the similar exposures; thus 400 mg Q6W is expected to be efficacious across indications.

TABLE 4

Summary of Pembrolizumab PK Exposure Metrics for the 400 mg Q6W Dosing Regimen Based on Simulations

| Alternative Dosing Regimen | Q6W 400 mg |
|---|---|
| Cavg, ss | |
| Relative to 200 mg Q3W, % difference in GM at steady state | 0.7% |
| Cmin, ss | |
| Relative to 2 mpk Q3W, % difference in GM at steady state | −12% |
| % of patients below lower limit of range for 200 mg and 2 mpk Q3W at steady state | <1% |
| Cmax, ss | |
| Relative to 10 mpk Q2W, % difference in GM at steady state | −66% |

Example 2

A Phase 1 Randomized Clinical Study of Pembrolizumab to Evaluate the Safety and Tolerability of Intravenous Infusion of 400 mg Pembrolizumab Q6W in Participants with Advanced Melanoma This study is designed to assess the pharmacokinetics (PK), safety and tolerability of pembrolizumab when administered every 6 weeks (Q6W). A cohort of 100 participants is given 400 mg pembrolizumab Q6W. PK, efficacy, and safety data are collected from this cohort of participants. Male/female participants of at least 18 years of age with advanced melanoma are enrolled in the study. No stratification based on age, sex, or other characteristics is used in this study.

Participants receive IV infusion of 400 mg pembrolizumab Q6W from cycles 1 to 18. PK, efficacy, and safety data are collected from these participants. Results provide preliminary PK, efficacy, and safety data of pembrolizumab when administered Q6W. Based on the robust understanding of pembrolizumab clinical pharmacology and its well-established E-R profiles, such a dosing schedule change is expected to produce similar efficacy and safety in all treatment settings where 200 mg Q3W pembrolizumab is approved (including monotherapy and in combination with other agents). Thus, a 400 mg Q6W regimen would have a similar benefit-risk profile to 200 mg Q3W, as a less frequent dosing regimen in the clinical use of pembrolizumab based on modeling and simulation analyses (see EXAMPLE 1).

Study Design

The study, which is a randomized, cross-over, multicenter, open-label, safety study of pembrolizumab in participants with advanced melanoma, is conducted in conformance with Good Clinical Practices (GCP). This Phase 1 study is conducted in participants with unresectable or metastatic melanoma. The treatment period continues every 42 days for up to 18 cycles (approximately 2 years). Treatment will continue as long as participants are receiving benefit from treatment and have not had disease progression or met any criteria for study withdrawal. In greater detail, the study consists of: (1) A screening period of up to a 28-day duration to ensure that the participant is eligible for the study and (2) an intervention period of approximately 104 weeks of treatment with pembrolizumab. Participants receive pembrolizumab via IV infusion over 30 minutes Q6W for up to 18 cycles, and (3) a follow-up period during which participants are monitored for AEs for 30 days and serious adverse events (SAEs) for 90 days (30 days if the participant initiates new anticancer therapy). Participants with an ongoing AE at the time of treatment discontinuation are followed until resolution, stabilization, the event is otherwise explained, or the participant is lost to follow-up.

Participants who discontinue for reasons other than radiographic disease progression have post-treatment follow-up imaging for disease status until disease progression is documented radiographically per RECIST 1.1 and, when clinically appropriate, confirmed by the site per iRECIST, initiating a non-study cancer treatment, withdrawing consent, becoming lost to follow-up or the end of the study. All participants are followed by telephone for overall survival in the Survival follow-up period until death, participant withdrawal of consent, becoming lost to follow-up or the end of the study.

All participants enrolled into this study will have a diagnosis of advanced melanoma. The results of this study will contribute to an understanding of the PK characteristics of pembrolizumab when administered in a Q6W dosing regimen. Safety parameters commonly used for evaluating investigational systemic anticancer treatments are included as safety endpoints including, but not limited to, the incidence of, causality, and outcome of adverse events (AEs)/serious adverse events (SAEs); and changes in vital signs and laboratory values. AEs will be assessed as defined by National Cancer Institute Common Terminology Criteria for Adverse Events [NCI CTCAE] Version 4.0).

An objective of this trial is to characterize the PK profile of pembrolizumab following administration as an IV infusion Q6W. PK data is analyzed after all participants complete Cycle 5. PK parameters include AUC, Cmax, and Cmin. Formation of Antidrug Antibodies (ADA) can potentially confound drug exposures at therapeutic doses and prime for subsequent infusion-related toxicity. Antidrug antibody response to pembrolizumab at the beginning of each of Cycles 1, 2, 4, and 5 are determined. Any impact of presence of ADAs on exposure of pembrolizumab is explored.

This study uses ORR based on RECIST 1.1 criteria as assessed by blinded independent central review (BICR) as the primary endpoint. Objective response rate is an acceptable measure of clinical benefit for a late stage study that demonstrates superiority of a new antineoplastic therapy, especially if the magnitude of the effect is large and the therapy has an acceptable risk/benefit profile. Images are submitted to an imaging CRO (iCRO) and read by independent central review blinded to treatment assignment to minimize bias in the response assessments.

Overall survival (OS) is a secondary endpoint and has been recognized as the gold standard for the demonstration of superiority of a new antineoplastic therapy in randomized clinical studies. RECIST 1.1 is used by the BICR when assessing images for efficacy measures and by the local site when determining eligibility. Modified RECIST 1.1 for immune-based therapeutics (iRECIST) assessment has been developed and published by the RECIST Working Group, with input from leading experts from industry and academia, along with participation from the US Food and Drug Administration and the European Medicines Agency. The unidimensional measurement of target lesions, qualitative assessment of non-target lesions, and response categories are identical to RECIST 1.1, until progression is seen by RECIST 1.1. However, if a participant is clinically stable, additional imaging may be performed to confirm radiographic progression. iRECIST is used by investigators to assess tumor response and progression and to make treatment decisions as well as for exploratory efficacy analyses where specified.

Inclusion Criteria

Participants are eligible to be included in the study only if all of the following criteria apply:

Participant has histologically or cytologically confirmed diagnosis of advanced melanoma Participant has unresectable Stage III or Stage IV melanoma, as per American Joint Committee on Cancer (AJCC) staging system not amenable to local therapy.

Participant is untreated for advanced or metastatic disease except as follows: BRAF V600 mutant melanoma may have received standard of care targeted therapy (e.g., BRAF/MEK inhibitor, alone or in combination) and be eligible for this study Prior adjuvant or neoadjuvant melanoma therapy is permitted if it was completed at least 4 weeks before randomization and all related AEs have either returned to baseline or stabilized (resolution of toxic effect(s) of the most recent prior therapy to Grade 1 or less [except alopecia]). If subject received major surgery or radiation therapy of >30 Gy, they must have recovered from the toxicity and/or complications from the intervention.

A female participant is eligible to participate if she is not pregnant, not breastfeeding, and agrees to follow specific contraceptive guidance during the treatment period and for at least 120 days or provides informed consent.

A participant should have an Eastern Cooperative Oncology Group (ECOG) performance status 0 (fully active, able to carry on all pre-disease performance without restriction) or 1 (restricted in physically strenuous activity but ambulatory and able to carry out work of alight or sedentary nature, e.g., light house work, office work) and should have adequate organ function as defined in Table 5. Specimens are collected within 72 hours prior to the start of study intervention.

TABLE 5

Adequate Organ Function Laboratory Values

| System | Laboratory Value |
|---|---|
| Hematological | |
| Absolute neutrophil count (ANC) | ≥1500/μL |
| Platelets | ≥100 000/μL |
| Hemoglobin | ≥9.0 g/dL or ≥5.6 mmol/L[1] |
| Renal | |
| Creatinine OR Measured or calculated[2] creatinine clearance (GFR can also be used in place of creatinine or CrCl) | ≤1.5 × ULN OR ≥30 mL/min for participant with creatinine levels >1.5 × institutional ULN |
| Hepatic | |
| Total bilirubin | ≤1.5 × ULN OR direct bilirubin ≤ULN for participants with total bilirubin levels >1.5 × ULN |
| AST (SGOT) and ALT (SGPT) | ≤2.5 × ULN (≤5 × ULN for participants with liver metastases) |
| Coagulation | |
| International normalized ratio (INR) OR prothrombin time (PT) Activated partial thromboplastin time (aPTT) | ≤1.5 × ULN unless participant is receiving anticoagulant therapy as long as PT or PTT is within therapeutic range of intended use of anticoagulants |

[1]Criteria must be met without erythropoietin dependency and without packed red blood cell (pRBC) transfusion within last 2 weeks.
[2]Creatinine clearance (CrCl) should be calculated per institutional standard.
ALT (SGPT) = alanine aminotransferase (serum glutamic pyruvic transaminase);
AST (SGOT) = aspartate aminotransferase (serum glutamic oxaloacetic transaminase);
GFR = glomerular filtration rate; ULN = upper limit of normal.

Exclusion Criteria

Participants are excluded from the study if any of the following criteria apply:

The participant is a woman of child-bearing potential (WOCBP) who has a positive urine pregnancy test within 72 hours prior to randomization or treatment allocation. If the urine test is positive or cannot be confirmed as negative, a serum pregnancy test is required.

The participant has received prior systemic treatment for unresectable or metastatic melanoma (except as noted in inclusion criteria described above).

The participant has received prior therapy with an anti-PD-1, anti-PD-L1, or anti-PD-L2 or with an agent directed to another stimulatory or co-inhibitory T-cell receptor (e.g., OX-40 and CD137) or any other antibody or drug specifically targeting checkpoint pathways other than anti-CTLA-4 which is permitted in the adjuvant setting.

The participant has received prior radiotherapy within 2 weeks of start of study treatment. Participants must have recovered from all radiation-related toxicities, not require corticosteroids, and not have had radiation pneumonitis.

The participant has received a live vaccine within 30 days prior to the first dose of study drug. Examples of live vaccines include, but are not limited to, the following: measles, mumps, rubella, varicella/zoster (chicken pox), yellow fever, rabies, Bacillus Calmette-Guerin (BCG), and typhoid vaccine. Seasonal influenza vaccines for injection are generally killed virus vaccines and are allowed; however, intranasal influenza vaccines (e.g., FluMist®) are live attenuated vaccines and are not allowed.

The participant is currently participating in or has participated in a study of an investigational agent or has used an investigational device within 4 weeks prior to the first dose of study intervention.

The participant has a diagnosis of immunodeficiency or is receiving chronic systemic steroid therapy (in dosing exceeding 10 mg daily of prednisone equivalent) or any other form of immunosuppressive therapy within 7 days prior the first dose of study drug.

The participant has a known additional malignancy that is progressing or has required active treatment within the past 2 years. Note: Participants with basal cell carcinoma of the skin, squamous cell carcinoma of the skin, or carcinoma in situ (e.g., breast carcinoma, cervical cancer in situ) that have undergone potentially curative therapy are not excluded.

The participant has known active CNS metastases and/or carcinomatous meningitis. Participants with previously treated brain metastases may participate provided they are radiologically stable, (i.e., without evidence of progression) for at least 4 weeks by repeat imaging (note that the repeat imaging should be performed during study screening), clinically stable and without requirement of steroid treatment for at least 14 days prior to first dose of study intervention.

The participant has severe hypersensitivity (≥Grade 3) to pembrolizumab and/or any of its excipients.

The participant has ocular melanoma.

The participant has an active autoimmune disease that has required systemic treatment in past 2 years (i.e., with use of disease modifying agents, corticosteroids or immunosuppressive drugs). Replacement therapy (e.g., thyroxine, insulin, or physiologic corticosteroid replacement therapy for adrenal or pituitary insufficiency) is not considered a form of systemic treatment and is allowed.

The participant has a history of (non-infectious) pneumonitis that required steroids or has current pneumonitis.

The participant has an active infection requiring systemic therapy.

The participant has a known history of human immunodeficiency virus (HIV) infection.

The participant has a known history of Hepatitis B (defined as Hepatitis B surface antigen [HBsAg] reactive) or known active Hepatitis C virus (defined as HCV RNA [qualitative] is detected) infection.

The participant has a history or current evidence of any condition, therapy, or laboratory abnormality that might confound the results of the study, interfere with the participant's participation for the full duration of the study, or is not in the best interest of the participant to participate, in the opinion of the treating investigator.

The participant has a known psychiatric or substance abuse disorder that would interfere with cooperating with the requirements of the study.

The participant is pregnant or breastfeeding or expecting to conceive or father children within the projected duration of the study, starting with the screening visit through 120 days after the last dose of study intervention.

Discontinuation of Study Intervention and Participant Withdrawal

Discontinuation of study intervention does not represent withdrawal from the study. As certain data on clinical events beyond study intervention discontinuation may be important to the study, they must be collected through the participant's last scheduled follow-up, even if the participant has discontinued study intervention. Therefore, all participants who discontinue study intervention prior to completion of the protocol-specified treatment period will still continue to participate in the study.

Participants may discontinue study intervention at any time for any reason or be dropped from the study intervention at the discretion of the investigator should any untoward effect occur. In addition, a participant may be discontinued from study intervention by the investigator if study intervention is inappropriate, the study plan is violated, or for administrative and/or other safety reasons.

A participant must be discontinued from study intervention but continue to be monitored in the study for any of the following reasons:

The participant or participant's legally acceptable representative requests to discontinue study intervention.

The participant interrupts study intervention administration for more than 12 consecutive weeks or has 3 cumulative missed doses.

The participant has a medical condition or personal circumstance which, in the opinion of the investigator, placed the participant at unnecessary risk from continued administration of study intervention.

The participant has a confirmed positive serum pregnancy test.

The participant has confirmed radiographic disease progression

The participant has any progression or recurrence of any malignancy, or any occurrence of another malignancy that requires active treatment The participant has unacceptable adverse experiences.

The participant has intercurrent illness other than another malignancy as noted above that prevents further administration of treatment.

Investigator decides to discontinue treatment.

The participant has recurrent Grade 2 pneumonitis

The participant has completed 35 treatments (approximately 2 years) with pembrolizumab A participant is withdrawn from the study if the participant or participant's legally acceptable representative withdraws consent from the study. If a participant withdraws from the study, they will no longer receive study treatment or be followed at scheduled protocol visits.

Informed Consent

The investigator or medically qualified designee obtains documented consent from each potential participant or each participant's legally acceptable representative prior to participating in a clinical study. If there are changes to the participant's status during the study (e.g., health or age of majority requirements), the investigator or medically qualified designee ensures the appropriate consent is in place.

Efficacy Assessments

Tumor assessments include all known or suspected disease sites. Imaging may include chest, abdomen, and pelvis computed tomography (CT) or magnetic resonance imaging (MRI) at baseline and when disease progression or brain metastases is suspected. Tumor imaging is strongly preferred to be acquired by CT. For chest, abdomen and pelvis, contrast-enhanced MRI may be used when CT with iodinated contrast is contraindicated, or when mandated by local practice. For the brain, MRI is the strongly preferred imaging modality.

The same imaging modality technique (ideally the same scanner, and consistent use of contrast) is used in a participant throughout the study. Consistent use of imaging techniques will help to optimize the reproducibility of the assessment of existing and new tumor burden, and to improve the accuracy of the assessment of response or progression. All scheduled images for all study participants are reviewed by the investigator for disease progression. In addition, images (including those obtained via other modalities) that are obtained at an unscheduled time point to determine disease progression (as well as imaging obtained for other reasons, but that capture radiologic progression based on investigator assessment), are also be filed at the study site.

Confirmation of measurable disease based on RECIST 1.1 by BICR at screening will be used to determine participant eligibility. Confirmation by the BICR that the participant's imaging shows at least 1 lesion that is appropriate for selection as a target lesion per RECIST 1.1 is required prior to participant allocation.

Initial Tumor Imaging

Initial tumor imaging at screening is performed within 28 days prior to the date of first dose. Any imaging obtained after Cycle 1 Day 1 of treatment is not included in the screening assessment. The site study team reviews screening images to confirm the participant has measurable disease per RECIST 1.1. If brain imaging is performed to document the stability of existing metastases, MRI is used if possible. If MRI is medically contraindicated, CT with contrast is an acceptable alternative.

Tumor Imaging During the Study

The first on-study imaging assessment is performed at 12 weeks (84 days ±7 days]) from the date of first dose. Subsequent tumor imaging is performed every 9 weeks (63 days±7 days) or more frequently if clinically indicated. After 52 weeks (365 days±7 days), participants who remain on treatment will have imaging performed every 12 weeks (84 days±7 days).

Objective response is confirmed by a repeat imaging assessment. Tumor imaging to confirm PR or CR is performed at least 4 weeks after the first indication of a response is observed. Participants will then return to regular scheduled imaging, starting with the next scheduled imaging time point. Participants who receive additional imaging for confirmation do not need to undergo the next scheduled tumor imaging if it is less than 4 weeks later; tumor imaging may resume at the subsequent scheduled imaging time point.

Per modified iRECIST, disease progression is confirmed by the site 4 to 8 weeks after first radiologic evidence of progressive disease (PD) in clinically stable participants. Participants who have unconfirmed disease progression may continue on treatment at the discretion of the investigator until progression is confirmed by the site. Participants who receive confirmatory imaging do not need to undergo the next scheduled tumor imaging if it is less than 4 weeks later; tumor imaging may resume at the subsequent scheduled imaging time point, if clinically stable. Participants who have confirmed disease progression by iRECIST, as assessed by the site, will discontinue study treatment.

End-of-Treatment and Follow-Up Tumor Imaging

For participants who discontinue study intervention, tumor imaging is performed at the time of treatment discontinuation (±4 week window). If previous imaging was obtained within 4 weeks prior to the date of discontinuation, then imaging at treatment discontinuation is not mandatory. For participants who discontinue study intervention due to documented disease progression, this is the final required tumor imaging if the investigator elects not to implement iRECIST.

For participants who discontinue study intervention without documented disease progression, every effort should be made to continue monitoring disease status by tumor imaging using the same imaging schedule used while on treatment every 12 weeks (±7 days) until the start of a new anticancer treatment, disease progression, pregnancy, death, withdrawal of consent, or the end of the study, whichever occurs first.

RECIST 1.1 Assessment of Disease

RECIST 1.1 is used as the primary measure for assessment of tumor response, date of disease progression, and as a basis for all protocol guidelines related to disease status (e.g., discontinuation of study intervention). Although RECIST 1.1 references a maximum of 5 target lesions in total and 2 per organ, this protocol allows a maximum of 10 target lesions in total and 5 per organ, if clinically relevant to enable a broader sampling of tumor burden. iRECIST Assessment of Disease iRECIST is based on RECIST 1.1, but adapted to account for the unique tumor response seen with immunotherapeutic drugs. iRECIST will be used by the investigator to assess tumor response and progression, and make treatment decisions. When clinically stable, participants are not discontinued until progression is confirmed by the investigator, working with local radiology. This allowance to continue treatment despite initial radiologic PD takes into account the observation that some participants can have a transient tumor flare in the first few months after the start of immunotherapy, and then experience subsequent disease response.

Any participant deemed clinically unstable is discontinued from study intervention at the time when site-assessed first radiologic evidence of PD, and is not required to have repeat tumor imaging for confirmation of PD by iRECIST. If the investigator decides to continue treatment, the participant may continue to receive study intervention and the tumor assessment should be repeated 4 to 8 weeks later to confirm PD by iRECIST, per investigator assessment. If repeat imaging does not confirm PD per iRECIST, as assessed by the investigator, and the participant continues to be clinically stable, study intervention continues and follows the regular imaging schedule. If PD is confirmed, participants are discontinued from study intervention.

If a participant has confirmed radiographic progression (iCPD), study intervention is discontinued; however, if the participant is achieving a clinically meaningful benefit, an exception to continue study intervention is considered. In this case, if study intervention is continued, tumor imaging continues to be performed. A summary of imaging and treatment requirements after first radiologic evidence of progression is provided in Table 6.

TABLE 6

Imaging and Treatment after First Radiologic Evidence of Progressive Disease

| | Clinically Stable | | Clinically Unstable | |
|---|---|---|---|---|
| | Imaging | Treatment | Imaging | Treatment |
| First radiologic evidence of PD by RECIST 1.1 per investigator assessment | Repeat imaging at 4 to 8 weeks to confirm PD | May continue study treatment at the assessment of the investigator and after the participant's consent | Repeat imaging at 4 to 8 weeks to confirm PD per investigator's discretion only. | Discontinue treatment |
| First radiologic evidence of PD by RECIST 1.1 | Repeat imaging at 4 to 8 weeks to confirm PD. | May continue study intervention at the investigator's discretion while awaiting confirmatory tumor imaging by site by iRECIST. | Repeat imaging at 4 to 8 weeks to confirm PD per investigator's discretion only. | Discontinue treatment |
| Repeat tumor imaging confirms PD (iCPD) by iRECIST per investigator assessment. | No additional imaging required. | Discontinue treatment. | No additional imaging required. | Not applicable |
| Repeat tumor imaging shows iUPD by iRECIST per investigator assessment. | Repeat imaging at 4 to 8 weeks to confirm PD. May occur at next regularly scheduled imaging visit. | Continue study intervention at the investigator's discretion. | Repeat imaging at 4 to 8 weeks to confirm PD per investigator's discretion only. | Discontinue treatment |
| Repeat tumor imaging shows iSD, iPR, or iCR by iRECIST per investigator assessment. | Continue regularly scheduled imaging assessments. | Continue study intervention at the investigator's discretion. | Continue regularly scheduled imaging assessments. | May restart study intervention if condition has improved and/or clinically stable per investigator's discretion. Next |

TABLE 6-continued

| Imaging and Treatment after First Radiologic Evidence of Progressive Disease | | | |
|---|---|---|---|
| Clinically Stable | | Clinically Unstable | |
| Imaging | Treatment | Imaging | Treatment |
| | | | tumor imaging should occur according to the regular imaging schedule. |

Abbreviations: iCPD = iRECIST confirmed progressive disease;
iCR = iRECIST complete response;
iPR = iRECIST confirmed partial response;
iRECIST = modified Response Evaluation Criteria in Solid Tumors 1.1 for immune-based therapeutics;
iSD = iRECIST stable disease;
iUPD = iRECIST unconfirmed progressive disease;
PD = progressive disease;
RECIST 1.1 = Response Evaluation Criteria in Solid Tumors 1.1;
VOP = verification of progression Safety Assessments Safety assessments include the collection of AEs and SAEs, monitoring of vital signs and laboratory assessments (including pregnancy tests), performance of electrocardiograms (ECGs) and physical examinations, and verification of concurrent medications.

Adverse Events

The investigator or qualified designee assesses each subject to evaluate for potential new or worsening AEs and more frequently if clinically indicated. Assessment of AEs includes, but is not limited to, the type, incidence, severity (graded by the National Cancer Institute Common Terminology Criteria for Adverse Events [NCI CTCAE] Version 4.0), timing, seriousness, and relatedness to study drug. Adverse events that occur during the study, including baseline signs and symptoms, are recorded.

Full Physical Examination

The investigator or qualified designee performs a complete physical exam during the Screening period. Clinically significant abnormal findings are recorded as medical history. After the first dose of study intervention, new clinically significant abnormal findings are recorded as AEs.

Directed Physical Examination

For cycles that do not require a full physical exam, the investigator or qualified designee performs a directed physical exam as clinically indicated prior to the administration of the study intervention. New clinically significant abnormal findings are recorded as AEs.

Vital Signs

Vital signs are measured in a semi-supine position after 5 minutes rest and include temperature, systolic and diastolic blood pressure, respiratory rate, pulse rate, and weight. Height is collected at screening only.

Electrocardiograms

A standard 12-lead ECG is performed using local standard procedures. Clinically significant abnormal findings at Screening are recorded as medical history. Additional ECG (s) are performed on study when clinically necessary. Clinically significant findings seen on the follow-up ECGs are recorded as AEs.

Clinical Safety Laboratory Assessments

The tests detailed in Table 7 are performed by a local laboratory. Additional tests may be performed at any time during the study as determined necessary by the investigator.

TABLE 7

| Protocol-Required Safety Laboratory Assessments | | | |
|---|---|---|---|
| Laboratory Assessments | | Parameters | |
| Hematology | Platelet Count | RBC Indices: | WBC count with |
| | RBC Count | MCV | Differential: |
| | Hemoglobin | MCH | Neutrophils |
| | Hematocrit | % Reticulocytes | Lymphocytes |
| | | | Monocytes |
| | | | Eosinophils |
| | | | Basophils |
| Chemistry | Blood Urea Nitrogen (BUN) | Potassium | Aspartate Aminotransferase (AST)/ Serum Glutamic-Oxaloacetic Transaminase (SGOT) | Total bilirubin (and direct bilirubin, if total bilirubin is elevated above the upper limit of normal) |

TABLE 7-continued

Protocol-Required Safety Laboratory Assessments

| Laboratory Assessments | Parameters | | | |
|---|---|---|---|---|
| | Albumin | Bicarbonate | Chloride | Phosphorous |
| | Creatinine | Sodium | Alanine Aminotransferase (ALT)/ Serum Glutamic-Pyruvic Transaminase (SGPT) | Total Protein |
| | Glucose | Calcium | Alkaline phosphatase | TSH Total T3 (or free T3) Total T4 (or free T4)a |
| Routine Urinalysis | Specific gravity pH, glucose, protein, blood, ketones, [bilirubin, urobilinogen, nitrite, leukocyte esterase] by dipstick Microscopic examination (if blood or protein is abnormal) | | | |
| Other Screening Tests | Follicle-stimulating hormone and estradiol (as needed in women of non-childbearing potential only) [Serum or urine] [alcohol and drug screen (to include at minimum: amphetamines, barbiturates, cocaine, opiates, cannabinoids and benzodiazepines) if applicable] [Serum or urine] β-human chorionic gonadotropin (β-hCG) pregnancy test (as needed for WOCBP) [Serology [(HIV antibody, hepatitis B surface antigen [HBsAg], and hepatitis C virus antibody)] [or specify other tests] [if applicable] | | | |

NOTES:
aT3 and T4 are preferred; if not available, free T3 and free T4 may be tested.
Abbreviations: β-hCG = β-human chorionic gonadotropin; ALT = alanine transaminase; AST = aspartate transaminase; BUN = blood urea nitrogen; HBsAg = hepatitis B surface antigen; HIV = human immunodeficiency virus; MCH = mean corpuscular hemoglobin; MCV = mean corpuscular volume; RBC = red blood cell; SGOT = serum glutamic oxaloacetic transaminase; SGPT = serum glutamic pyruvic transaminase; TSH = thyroid stimulating hormone; WBC = white blood cell; WOCBP = woman/women of childbearing potential.

Time Period and Frequency for Collecting AE, SAE, and Other Reportable Safety Event Information All AEs, SAEs, and other reportable safety events that occur after the consent form is signed but before treatment allocation/randomization must be reported by the investigator if the participant is receiving placebo run-in or other run-in treatment, if the event cause the participant to be excluded from the study, or is the result of a protocol-specified intervention, including but not limited to washout or discontinuation of usual therapy, diet, or a procedure. All AEs from the time of treatment allocation/randomization through 30 days following cessation of study intervention must be reported by the investigator.

All AEs meeting serious criteria, from the time of treatment allocation/randomization through 90 days following cessation of study intervention or 30 days following cessation of study intervention if the participant initiates new anticancer therapy, whichever is earlier, must be reported by the investigator. Additionally, any SAE brought to the attention of an investigator at any time outside of the time period specified above is reported immediately if the event is considered drug-related.

Statistical Methods for Efficacy Analyses

Objective Response Rate (ORR)—ORR is calculated as the ratio of the number of participants reported to have achieved a confirmed CR or PR verified by BICR, divided by the number of participants included in APaT population. Participants in the APaT analysis population without ORR assessments will be counted as non-responders. A 95% exact binomial CI (based on method Clopper and Pearson, 1934) is calculated for the true ORR.

Progression-Free Survival (PFS)— The non-parametric Kaplan-Meier method is used to estimate the PFS distribution. 95% CIs for the median PFS and PFS point estimates at various follow-up times from first day of study treatment will be calculated. Since disease progression is assessed periodically, PD can occur any time in the time interval between the last assessment where PD was not documented and the assessment when PD is documented. The true date of PD will be approximated by the date of the first assessment at which PD is objectively documented based on RECIST 1.1 by BICR. Death is always considered as a PFS event. Participants who do not experience a PFS event will be censored at the last disease assessment. For the analysis of PFS, if the events (PD or death) are immediately after more than one missed disease assessment, the data are censored at the last disease assessment prior to missing visits. Also, data after new anticancer therapy are censored at the last disease assessment prior to the initiation of new anticancer therapy. If a participant meets multiple criteria for censoring, the censoring criterion that occurs earliest will be applied.

Overall Survival (OS)— The non-parametric Kaplan-Meier method is used to estimate the OS distribution. 95% CIs for the median OS and OS point estimates at various follow-up times from first day of study treatment is calculated.

Duration of Response (DOR)—DOR is summarized descriptively using the non-parametric Kaplan-Meier method. Only the subset of participants who show a CR or PR are included in this analysis.

Analysis Strategy for Key Efficacy Endpoint

Table 8 summarizes the primary analysis approach for key efficacy endpoints.

TABLE 8

Analysis Strategy for Key Efficacy Endpoints

| Endpoint | Statistical Method | Analysis Population | Missing Data Approach |
|---|---|---|---|
| Primary Endpoints | | | |
| ORR per RECIST 1.1 by BICR | Exact method based on binomial distribution (Clopper-Pearson method) | APaT | Participants without assessments are considered non-responders and conservatively included in the denominator |
| Key Secondary Endpoint | | | |
| PFS per RECIST 1.1 by BICR | Summary statistics using Kaplan-Meier method | APaT | Primary censoring rule |
| OS | Summary statistics using Kaplan-Meier method | APaT | Censored at the last known alive date |
| DOR per RECIST 1.1 by BICR | Summary statistics using Kaplan-Meier method | APaT | Non-responders are excluded from analysis. Responders are censored according to the censoring rules. | a Statistical models are described in further detail in the text.
Abbreviations: APaT = All Participants as Treated;
BICR = blinded independent central review;
DOR = duration of response;
ORR = objective response rate;
OS = overall survival;
PFS = progression-free survival;
RECIST = Response Evaluation Criteria in Solid Tumors Statistical Methods for Safety Analyses Safety and tolerability are assessed by clinical review of all relevant parameters including adverse experiences and laboratory parameters. The broad AE categories consisting of the percentage of participants with any AE, a drug-related AE, a serious AE, an AE which is both drug-related and serious, and who discontinued due to an AE are summarized via point estimates with 95% CIs (Table 9).

TABLE 9

Analysis Strategy for Safety Parameters

| Safety Endpoint | Within Group 95% CI | Descriptive Statistics |
|---|---|---|
| Any AE | X | X |
| Any Serious AE | X | X |
| Any Drug-related AE | X | X |
| Any Serious and Drug-related AE | X | X |
| Discontinuation due to AE | X | X |
| Specific AEs, SOCs, or PDLCs | | X |
| Change from Baseline Results (Labs, Vital Signs) | | X |

Note:
95% CIs will be calculated using the Clopper Pearson method
X = results are provided
Abbreviations: SOC = System Organ Class;
PDLC = Pre-Defined Limit of Change An AE is any untoward medical occurrence in a clinical study participant, temporally associated with the use of study intervention, whether or not considered related to the study intervention. An AE can therefore be any unfavorable and unintended sign (including an abnormal laboratory finding), symptom, or disease (new or exacerbated) temporally associated with the use of the drug. The following are included as AEs:

Any abnormal laboratory test results (hematology, clinical chemistry, or urinalysis) or other safety assessments (e.g., ECG, radiological scans, vital signs measurements), including those that worsen from baseline, or are considered clinically significant in the medical and scientific judgment of the investigator.

Exacerbation of a chronic or intermittent pre-existing condition including either an increase in frequency and/or intensity of the condition.

New conditions detected or diagnosed after study intervention administration even though it may have been present before the start of the study.

Signs, symptoms, or the clinical sequelae of a suspected drug-drug interaction.

Signs, symptoms, or the clinical sequelae of a suspected overdose of either study intervention or a concomitant medication.

Worsening of signs and symptoms of malignancy during the study is reported as an AE.

Disease progression assessed by measurement of malignant lesions on radiographs or other methods are not be reported as an AE, unless the event results in hospitalization or death.

The following events do not meet the AE definition for purposes of this study:

Medical or surgical procedure (e.g., endoscopy, appendectomy): the condition that leads to the procedure is the AE.

Situations in which an untoward medical occurrence did not occur (social and/or convenience admission to a hospital).

Anticipated day-to-day fluctuations of pre-existing disease(s) or condition(s) present or detected at the start of the study that do not worsen.

Surgery planned prior to informed consent to treat a pre-existing condition that has not worsened.

If an event is not an AE per definition above, then it cannot be an SAE even if serious conditions are met. An SAE is defined as any untoward medical occurrence that, at any dose:

Results in death

Is life-threatening. The term "life-threatening" in the definition of "serious" refers to an event in which the participant was at risk of death at the time of the event. It does not refer to an event, which hypothetically might have caused death, if it were more severe.

Requires inpatient hospitalization or prolongation of existing hospitalization. Hospitalization is defined as an inpatient admission, regardless of length of stay, even if the hospitalization is a precautionary measure for continued observation. Hospitalization for an elective procedure to treat a pre-existing condition that has not worsened is not an SAE. A pre-existing condition is a clinical condition that is diagnosed prior to the use of an MSD product and is documented in the participant's medical history.

Results in persistent or significant disability/incapacity. The term disability means a substantial disruption of a person's ability to conduct normal life functions. This definition is not intended to include experiences of relatively minor medical significance such as uncomplicated headache, nausea, vomiting, diarrhea, influenza, and accidental trauma (e.g., sprained ankle) that may interfere with or prevent everyday life functions but do not constitute a substantial disruption.

Is a congenital anomaly/birth defect in offspring of participant taking the product regardless of time to diagnosis.

Medical or scientific judgment is exercised in deciding whether SAE reporting is appropriate in other situations such as important medical events that may not be immediately life-threatening or result in death or hospitalization but may jeopardize the participant or may require medical or surgical intervention to prevent one of the other outcomes listed in the above definition. These events are usually considered serious. Examples of such events include invasive or malignant cancers, intensive treatment in an emergency room or at home for allergic bronchospasm, blood dyscrasias or convulsions that do not result in hospitalization, or development of drug dependency or drug abuse.

Demographics and Baseline Characteristics

The number and percentage of subjects screened, allocated, the primary reasons for screening failure, and the primary reasons for discontinuation are displayed. Demographic variables (e.g., age, gender), baseline characteristics, primary and secondary diagnoses, and prior and concomitant therapies is summarized either by descriptive statistics or categorical tables for all enrolled subjects.

Subgroup Analyses

To determine whether the response rate is consistent across various subgroups, the estimate of the response rate (with a nominal 95% CI) for the primary endpoint is estimated within each category of the following classification variables:

Age category (<65 vs. ≥65 years)
Sex (female vs. male)
Race (white vs. non-white)
Disease stage (II vs. IVM1a vs. IVM1b vs IVM1c)
Brain metastasis (yes vs. no)
ECOG status (0 vs. 1)
PD-L1 status (positive vs. negative)
BRAF wild type versus BRAF mutant (no prior treatment) versus BRAF mutant (prior treatment)

A Forest plot is produced, which provides the estimated point estimates and CIs for the treatment effect across the categories of subgroups listed above. Any specified subgroups that have less than 10 participants are excluded from analysis.

All references cited herein are incorporated by reference to the same extent as if each individual publication, database entry (e.g. Genbank or GeneID entries), patent application, or patent, was specifically indicated to be incorporated by reference. This statement is intended by Applicants, pursuant to 37 C.F.R. § 1.57(b)(1), to relate to each and every individual publication, database entry (e.g. Genbank or GeneID entries), patent application, or patent, each of which is clearly identified in compliance with 37 C.F.R. § 1.57(b)(2), even if such citation is not immediately adjacent to a dedicated statement of incorporation by reference. Citation of the references herein is not intended as an admission that the reference is pertinent prior art, nor does it constitute any admission as to the contents or date of these publications or documents.

What is claimed is:

1. A method of treating cancer in a human patient comprising administering 400 mg of pembrolizumab to the patient every approximately six weeks.

2. The method of claim 1, wherein the cancer is selected from the group consisting of: melanoma, non-small cell lung cancer, head and neck cancer, urothelial cancer, breast cancer, gastric cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, endometrial cancer, squamous cell carcinoma, Merkel cell carcinoma and salivary cancer.

3. The method of claim 1, wherein the patient has a tumor with a high mutational burden.

4. The method of claim 1, wherein the patient has a microsatellite instability-high (MSI-H) or mismatch repair deficient solid tumor.

5. The method of claim 1, wherein the cancer is melanoma.

6. The method of claim 1, wherein the cancer is non-small cell lung cancer.

7. The method of claim 1, wherein the cancer is head and neck cancer.

8. The method of claim 2, wherein the Hodgkin lymphoma is classical Hodgkin lymphoma cancer.

9. The method of claim 1, wherein the cancer is urothelial cancer.

10. The method of claim 1, wherein the cancer is colorectal cancer.

11. The method of claim 1, wherein the cancer is gastric cancer.

12. The method of claim 1, wherein the cancer is esophageal cancer.

13. The method of claim 1, wherein the cancer is cervical cancer.

14. The method of claim 1, wherein the cancer is hepatocellular cancer.

15. The method of claim 1, wherein the cancer is Merkel cell carcinoma.

16. The method of claim 1, wherein the cancer is renal cancer.

17. The method of claim 1, wherein the cancer is endometrial cancer.

18. The method of claim 1, wherein the cancer is breast cancer.

19. The method of claim 5, wherein the cancer is unresectable or metastatic melanoma.

20. The method of claim 7, wherein the cancer is recurrent or metastatic head and neck squamous cell cancer (HNSCC).

21. The method of claim 1, wherein the cancer is (1) refractory classical Hodgkin lymphoma (cHL), or (2) cHL and the patient has relapsed after 3 or more lines of therapy for cHL.

22. The method of claim 9, wherein the cancer is locally advanced or metastatic urothelial carcinoma.

23. The method of claim 1, wherein the cancer is locally advanced or metastatic gastric cancer or gastroesophageal junction adenocarcinoma.

24. The method of claim 1, wherein the cancer is resected high-risk stage III melanoma.

25. The method of claim 1, wherein the cancer is hepatocellular carcinoma (HCC).

26. The method of claim 1, wherein the cancer is renal cell carcinoma (RCC).

27. The method of claim 1, wherein the cancer is recurrent, locally advanced or metastatic Merkel cell carcinoma (MCC).

28. The method of claim 1, wherein the cancer is squamous cell carcinoma.

* * * * *